(12) United States Patent
Baulieu et al.

(10) Patent No.: US 9,339,508 B2
(45) Date of Patent: May 17, 2016

(54) USE OF 3-METHOXY-PREGNENOLONE FOR THE PREPARATION OF A DRUG FOR TREATING A TRAUMATIC BRAIN INJURY

(71) Applicant: MAPREG, Le Kremlin Bicetre (FR)

(72) Inventors: Etienne-Emile Baulieu, Neuilly-sur-Seine (FR); Esther Fellous, Paris (FR); Paul Robel, Paris (FR)

(73) Assignee: MAPREG, Le Kremlin Bicetre (FR)

( * ) Notice: Subject to any disclaimer, the term of this patent is extended or adjusted under 35 U.S.C. 154(b) by 287 days.

(21) Appl. No.: 13/666,663

(22) Filed: Nov. 1, 2012

(65) Prior Publication Data

US 2013/0244991 A1  Sep. 19, 2013
US 2014/0045807 A2  Feb. 13, 2014
US 2014/0228336 A2  Aug. 14, 2014

Related U.S. Application Data

(63) Continuation-in-part of application No. 12/232,993, filed on Sep. 26, 2008, now Pat. No. 8,334,278, which is a continuation-in-part of application No. 10/542,495, filed as application No. PCT/FR2004/000086 on Jan. 16, 2004, now Pat. No. 8,034,798.

(30) Foreign Application Priority Data

Jan. 17, 2003 (FR) ...................................... 0300507

(51) Int. Cl.
A61K 31/56 (2006.01)
A01N 45/00 (2006.01)
A61K 31/57 (2006.01)
A61K 31/58 (2006.01)

(52) U.S. Cl.
CPC ................. *A61K 31/57* (2013.01); *A61K 31/58* (2013.01)

(58) Field of Classification Search
CPC .............................. A61K 31/56; A61K 31/57
USPC .................................................. 514/169, 182
See application file for complete search history.

(56) References Cited

U.S. PATENT DOCUMENTS 6,245,757 B1 * 6/2001 Chopp et al. ................... 514/177
2002/0072509 A1 * 6/2002 Stein et al. ..................... 514/169

FOREIGN PATENT DOCUMENTS

EP  1 310 258 A1  5/2003
WO  WO 01/68068 A2  9/2001
WO  WO 02/36128 A1  5/2002

OTHER PUBLICATIONS

Kolb et al., Nerve Growth Factor Treatment Prevents Dendritic Atrophy and Promotes Recovery of Function After Cortical Injury, Neuroscience, vol. 76, No. 4, pp. 1139-1151, (1996).
Zhang et al., "Cytoskeletal Disruption Following Contusion Injury to the Rat Spinal Cord", Journal of Neuropathology and Experimental Neurology. vol. 59, No. 4, pp. 287-296, (2000).
Schumacher et al., "Pretreatment with Calpain Inhibitor CPE-4143 Inhibits Calpain I Activation and Cytoskeletal Degradation, Improves Neurological Function, and Enhances Axonal Survival After Traumatic Spinal Cord Injury". Journal of Neurochemistry, vol. 74, No. 4, pp. 1646-1655, (2000).
Springer et al., "Rapid Calpain I Activation and Cytoskeletal Protein Degradation Following Traumatic Spinal Cord Injury: Attenuation with Riluzole Pretreatment", Journal of Neurochemistry, vol. 69, No. 4, pp. 1592-1600, (1997).
Matus, "MAP2", Microtubules, pp. 155-166, (1994).
Sanchez et al., "Phosphorylation of Microtubule-Associated Protein 2 (MAP2) and its Relevance for the Regulation of the Neuronal Cytoskeleton Function", Progress in Neurobiology, vol. 61, pp. 133-168, (2000).
Caceres, et al., "Suppression of MAP2 in Cultured Cerebeller Macroneurons Inhibits Minor Neurite Formation", Neuron, vol. 9, pp. 607-618, (1992).
Harada et al., "MAP2 is Required for Dendrite Elongation, PKA Anchoring in Dendrites, and Proper PKA Signal Transduction", The Journal of Cell Biology, vol. 158, No. 3, pp. 541-549, (2002).
Reyna-Neyra et al., "Estradiol and Progesterone Modify Microtubule Associated Protein 2 Content in the Rat Hippocampus", Brain Research Bulletin, vol. 58. No. 6, pp. 607-612, (2002).
Nakatomi et al., "Regeneration of Hippocampal Pyramidal Neurons after Ischemic Brain Injury by Recruitment of Endogenous Neural Progenitors", Cell. vol. 110, pp. 429-441. (2002).
Garcia-Estrada et al., "Dehydroeplandrosterone, Pregnenolone and Sex Steroids Down-Regulate Reactive Astroglia in the Male Rat Brain after a Penetrating Brain Injury", Int. J. Devl. Neuroscience, vol. 17, No. 2, pp. 145-150, (1999).
Legrand et al., "Pregnenolone Reverses the Age-Dependent Accumulation of Glial Fibrillary Acidic Protein within Astrocytes of Specific Regions of the Rat Brain". Brain Research, vol. 802, pp. 125-132, (1998).
Guth et al., "Key Role for Pregnenolone in Combination Therapy that Promotes Recovery after Spinal Cord Injury", Proc. Natl. Acad. Sci. USA, vol. 91, pp. 12308-12311, (1994).
Gursoy et al., "Pregnenolone Protects Mouse Hippocampal (HT-22) Cells Against Glutamate and Amyloid Beta Protein Toxicity", Neurochemical Research, vol. 26, No. 1, pp. 15-21, (2001).

(Continued)

*Primary Examiner* — Sue Liu
*Assistant Examiner* — Helen Chui
(74) *Attorney, Agent, or Firm* — Finnegan, Henderson, Farabow, Garrette and Dunner, L.L.P.

(57) ABSTRACT

A method for the treatment of a traumatic brain lesion comprises administering to the patient an effective quantity of 3Ǝ-methoxy-pregna-5-ene-20-one (3Ǝ-methoxy-PREG).

6 Claims, 27 Drawing Sheets

(56) References Cited

OTHER PUBLICATIONS

Parveen Sra et al., "Evaluation of Locomotor Rating Scales Following Spinal Cord Injury in Rats", Orthopaedic Research Society, Feb. 1-4, 1999, p. 982, Anaheim, California.

S. W. Scheff, "A statistical method for analyzing rating scale data: the BBB locomotor score", J. Neurotrauma, Oct. 19, 2002, pp. 1251-1260, Lexington, Kentucky.

D. M. Basso et al., "A sensitive and reliable locomotor rating scale for open field testing in rats", J. Neurotrauma, Feb. 12, 1995, pp. 1-21, Columbus, Ohio.

D. M. Basso et al., "MASCIS evaluation of open field locomotor scores: effects of experience and teamwork on reliability. Multicenter Animal Spinal Cord Injury Study", J. Neurotrauma, Jul. 13, 1996, pp. 343-359, Columbus, Ohio.

Murakami et al., "Pregnenolone Binds to Microtubule-Associated Protein 2 and Stimulates Microtubule Assembly", PNAS, vol. 97, No. 7, pp. 3579-3584 (2000).

Campbell et al., The role of the hippocampus in the pathophysiology of major depression, (2004) J Psychiatry Neurosci 29(6):417-26.

Fontaine-Lenoir et al., Microtubule-associated protein 2 (MAP2) is a neurosteroid receptor, (2006) PNAS 103;4711-4716.

Bianchi et al., Neuronal Plasticity, Stress and Depression: Involvement of the Cytoskeletal Microtubular System, (2005) Current Drug Targets—CNS & Neurological Disorders 4, 597-611.

Bianchi et al., Isolation rearing induces recognition memory deficits accompanied by cytoskeletal alterations in rat hippocampus, (2006) European Journal of Neuroscience vol. 24, 2894-2902.

Bianchi et al., Cytoskeletal Changes in the Hippocampus Following Restraint Stress: Role of Serotonin and Microtubules, (2003) SYNAPSE 49:188-194.

Bianchi et al., Fluoxetine Administration Modulates the Cytoskeletal Microtubular System in the Rat Hippocampus, (2009) SYNAPSE 63:359-364.

Meieran et al., Chronic pregnenolone effects in normal humans: attenuation of benzodiazepine-induced sedation, (2004) Psychoneuroendocrinology 29, 486-500.

Miyamoto et al., Effects of long-term treatment with desipramine on microtubule proteins in rat cerebral cortex, (1997) European Journal of Pharmacology 333, 279-287.

Murakami et al., Pregnenolone binds to microtubule-associated protein 2 and stimulates microtubule assembly, (2000) PNAS Mar. 28, 2000 vol. 97 No. 7:3579-3584.

Donati et al., Chronic Antidepressant Treatment Prevents Accumulation of Gsα in Cholesterol-Rich, Cytoskeletal-Associated, Plasma Membrane Domains (Lipid Rafts), (2005) Neuropsychopharmacology 30, 1238-1245.

Serra, et al., Social isolation-induced increase in the sensitivity of rats to the steriodogenic effect of ethanol, (2003) Journal of Neurochemistry 85, 257-263.

Warner-Schmidt, et al., Hippocampal Neurogenesis: Opposing Effects of Stress and Antidepressant Treatment, (2006) Hippocampus 16:239-249.

* cited by examiner

NGF

NGF + Preg

NGF + 43B

USE OF 3-METHOXY-PREGNENOLONE FOR THE PREPARATION OF A DRUG FOR TREATING A TRAUMATIC BRAIN INJURY

CROSS-REFERENCES TO RELATED APPLICATIONS

This application is a continuation-in-part of, and claims priority from, U.S. Ser. No. 12/232,903 filed Sep. 26, 2008, which is a continuation-in-part of, and claims priority from, U.S. Ser. No. 10/542,495 filed Jul. 15, 2005, which claims priority under 35 U.S.C. 371 from PCT/FR04/00086 filed on Jan. 16, 2004, which claims priority from French application No-0300507 filed on Jan. 17, 2003. The content of each of the prior applications are incorporated herein by reference.

TECHNICAL FIELD

The invention involves an innovative use of neurosteroid derivatives, notably pregnenolone and pregnenolone derivatives, to treat nervous system lesions, in particular a traumatic spinal cord or brain lesion, and certain neurodegenerative diseases, notably linked to the ability of the aforementioned neurosteroid derivatives to stabilize and/or increase the polymerization of neuronal microtubules. The invention further relates to the therapeutic use of particular pregnenolone derivatives for treating depressive disorders.

BACKGROUND ART

Neurodegenerative diseases and CNS lesions such as spinal cord and brain injuries are widespread conditions with devastating effects on the life of the patients and their close relatives. As an example, about 450,000 people in the USA live with spinal cord injury (1 in 670) and only 5% of patients with complete injury recover locomotion. Almost more dramatically, about 2,000,000 US people undergo each year a traumatic brain injury (TBI), whose immediate as well as long term consequences are largely underestimated and deprived of medical solution, TBI provokes traumatic lesions of the brain that occur through a direct or indirect physical impact, either focal or diffuse like a blast an explosion. Long term consequences of TBI include mood disorders, sleep disorders, cognitive memory loss, locomotor disabilities and occur very frequently unrespectively of the initial severity of the trauma, racing an increasing number of helpless brain post-traumatic situations in soldiers back from battle field, the US government recently declared traumatic brain injury as a real epidemy and a major orphan sector.

At the biological level, TBI provokes widespread shearing and stretching of nerve fibers (diffuse axonal injury) and leads to destabilization of neuronal microtubules, disruption of the cytoskeleton, dendrite atrophy and loss of MAPs. These damages are important contributors to the functional impairments after TBI because microtubules, neurofilaments and microfilaments of the neuronal cytoskeleton are essential for the physiological functions of the neuronal cell. The functional consequences of dendritic damage are reflected in reports of compromised efficacy of synaptic transmission following TBI. After TBI, a spontaneous and partial recovery of lost function can occur over time although axonal regeneration is extremely limited in the mammalian adult central nervous system. The underlying mechanisms of this recovery are not fully understood but they involve the reorganization of connectivity with the formation of new synapses between neurons (Thompson et al., 2006). These observations have important therapeutic implications in humans, and were part of the inventor's strategy to develop therapies that stimulate plasticity to maximize the recovery of function.

Despite many research efforts in the field, effective molecules for the treatment of neurodegenerative diseases and CNS lesions are still not available. Interestingly, neurodegenerative diseases and CNS lesions share many pathogenetical similarities including deterioration of neuronal cytoskeleton. This deterioration can be the consequence but also the cause of damage to the affected cells. Growing evidence suggest that the cytoskeletal degradation observed after spinal cord injury (Zhang et al., *J. Neuropathol Exp Neurol* 2000) results from increased extracellular glutamate which in turn increases intracellular $Ca^{++}$ activation of ion channels. Thus, the accumulation of intracellular $Ca^{++}$ (i.e. $Ca^{++}$ overload) can activate the protease calpain which induces proteolysis of MAP2 and TAU leading to abnormal microtubule depolymerization. The use of a calpain inhibitor (Schumacher et al., *J Neurochem* 2000) and the salting-out of glutamate (Springer et al., *J Neurochem* 2997) decrease the consequences of spinal cord injury in rodents by partially preserving the cytoskeleton.

Mood disorders include major and bipolar depression and are common, chronic and life threatening illnesses in Western society (Maris, *Lancet* 2002). Major depression affects 8-12% of the population (Andrade et al., *Int. J. Meth. Psychiatr. Res.* 2003) and 15% of suicides are committed by depressives in the USA (Manji et al., *Nat. Med.* 2001). Major depression is traditionally associated with low levels of the central nervous system (CNS) monoamines (i.e. serotonin [5-HT], dopamine [DA], norepinephrine [NE]). Antidepressant drugs target monoaminergic function by preventing their reuptake presynaptically cc blocking their metabolism. Although antidepressants seem to exert their initial effect by immediately increasing monoaminergic levels intrasynaptically (Malaglè et al., *Eur. J. Pharmacol.* 1995; Romero et al., *J. Neurochem.* 1996) their clinical efficacy occurs only after chronic administration (Blier and de Montigny, *TiPS* 1994). These findings lead the scientific community to the novel hypothesis that enhanced monoaminergic neurotransmission per se is not sufficient to explain the clinical actions of antidepressant drugs (Warner-Schmidt and Duman, *Hippocampus* 2006). Recently, magnetic resonance studies showed volume loss and structural abnormality in the hippocampus of depressed individuals (Campbell and Macqueen, *J. Psychiatry Neurosci,* 2004). Stress and major depression appear to be closely related and pre-clinical studies employing stress as predisposing factor to depression suggest that the hippocampal structural alterations observed in depressed patients may result from dendritic atrophy, neuriteal alterations, structural glial changes and neurogenesis decrease (Warner-Schmidt and Duman, *Hippocampus* 2006). Importantly, chronic treatment with antidepressant drugs seems to prevent stress-induced neuronal plasticity alterations in rodents (Warner-Schmidt and Duman, *Hippocampus* 2006). Consequently, the pathogenesis of depression may also involve stress-induced structural alterations in specific brain regions with the same features of dendrite alterations and impaired neurogenesis. The dynamics of the cytoskeletal microtubular system are fundamental for the formation and maintenance of synaptic connectivity including remodeling and extension of neurites (Mitchison and Kirschner, *Neuron* 1988) and dendrites (Valliant at al, neuron 2002). Microtubules are formed by the polymerization of the tubulin α/β heterodimers and in higher vertebrates three α-tubulins (α1, α2, and α4) and five β-tubulin (βI, βII, βIII, βIVα and βIVb) isotypes are specifically expressed in the brain (Luduena, *Int. Rev. Cytol.* 1998). Microtubules specifically interact with different proteins named microtubule-associated proteins (MAPs), between them the microtubule-associated protein 2 (MAP2) isoforms and TAO represent the major components of the proteins interacting with neuronal microtubules. They are present in all the extensions which constitute the dendritic arborization of a neuron, such neuronal branches are a key factor for the establishment of synaptic connections (Matus, *Microtubules* 1994; Sanchez et al., *Prog. Neurobiol* 2000). MAP2 proteins are necessary for the formation of dendrites since suppression of MAP2 synthesis caused either neuritic growth to stop in neurons in culture (Caceres et al. *Neuron* 1992) or dendritic growth to stop in MAP2 knockout mice (Harada et al., *J. Cell. Biol.* 2002). However, the synthesis of MAP2 proteins is not in and of itself sufficient to induce this dendritic growth process. Certain steroids such as estradiol or progesterone can induce an increase in MAP2 synthesis without . . . inducing significant morphological changes (Reyna-Neyra at al., *Brain Res.* 2002). Recent data showed that experimental models of stress and depression such as restraint stress (Bianchi et al. *Synapse* 2003), forced swimming test (Bianchi at al., *Curr. Drug Targets CNS Neurol. Disord.* 2005) and social isolation (Bianchi et al., *EJN* 2006) induce abnormal microtubule stabilization and dendrite retraction in rat hippocampus. Additionally, different stressors and administration of glucocorticoids can change the expression of different MAPs including MAP-2, MAP-1A and TAU in rat hippocampus (for an extensive review see Bianchi et al., *Curr. Drug Targets CNS Neurol. Disord.* 2005).

Finally, antidepressant drugs can affect MAP2 function and in turn the dynamics of the microtubular system. Indeed, both 5-HT and NP reuptake inhibitors differentially increased MAP2 phosphorylation and decreased microtubule assembly (i.e. increased microtubule dynamics) in rat cerebral cortex (Perez at al., *Neuropsychopharmacology* 1991; Miyamoto et al., *Eur. J. Pharmacol.,* 1997) and in neuroblastoma cells (Donati and Rasenick, *Neuropsychopharmacology* 2005). Taken all together, these findings lead to the original hypothesis that the pathogenesis and treatment of depression may include changes in microtubule dynamics (Bianchi et al., *Curr. Drug Targets CNS Neurol. Disord.* 2005).

Neurodegenerative disorders, traumatic brain and spinal cord injuries and depressive disorders thus share alterations in microtubules dynamics and MAP2 expression and function-Importantly, the MAP2/TAU loss and microtubule depolymerization observed in spinal cord and brain injury can be directly responsible for the dysfunction of certain neurons and can result in their death. Moreover, such cytoskeletal deterioration can affect the number and the length of the dendritic extensions of the remaining neuronal cells and, as a consequence, decreases their effectiveness. Consistently, treatment with nerve growth factor (NGF), which prevents dendritic atrophy, enables better functional recovery after a lesion of the cerebral cortex in the rat (Kolb et al., *Neuroscience* 1997).

The existence of stem cells in certain regions of the central nervous system is well established today. Lesions stimulate the proliferation of these cells. However, these cells must migrate and differentiate. Differentiation implies, at a fundamental level, the development of the cytoskeleton.

It has been shown recently that, after cerebral ischemia, stem cells could differentiate into neurons and become integrated into the existing neuronal circuits (Nakatomi et al, *Cell* 2002). Similarly, it is well established that antidepressant drugs stimulate neurogenesis in the sub-granular zone of adult hippocampus and newborn cell migrate to the granule cell layer to become mature neurons extending dendrites and neurites (Warner-Schmidt and Duman, *Hippocampus* 2006).

The stimulation of dendrite and/or neurite growth (neuronal branching outgrowth) in these stem cells, and in already existing mature neurons, by molecules that improve tubulin polymerization and microtubule function could increase and or recover the number of functional synaptic connections.

Pregnenolone (PREG) binds to MAP2 and has the extremely important and original property of reinforcing the activity of this protein, namely its role in the activation of the tubulin polymerization process and the establishment of microtubular structures of greater function (Murakami et al., *Proc Natl Acad Sci USA* 2000).

In spite of much research, at present no specific targets other than MAPs have been identified for PREG.

MAP2 protein is found primarily in neurons. It is therefore probable that MAP2 binding molecules mainly target the cells of the nervous system, without having a notable action on other cellular types in which the concentration of MAP2 is very low.

Studies that demonstrate an in vivo effect by PREG are very few but they suggest a beneficial role for this steroid. It was shown that PREG administration decreased the reaction (formation of gliotic tissue (i.e. accumulation of astrocytes)) following a penetrating lesion in rat cerebral cortex and hippocampus (Garcia-Estrada et al, *Int. J Devl Neuroscience* 1999). Additionally, PREG administration reverses the age-dependent accumulation of glial fibrillary acidic protein within astrocytes of specific regions of the rat brain (Legrand and Alonso, *Brain Res.* 1998), PREG also contributed to improved functional recovery after a spinal cord trauma (Guth et al., *Proc Natl Acad Sci USA* 1994). Furthermore, PREG was showed to protect against toxicity induced by glutamate and the protein beta amyloid in hippocampal cells line (HT-22) cultures (Gursoy et al., *Neurochem Res.* 2001).

On the other hand, decreased levels of PREG have been reported in the cerebrospinal fluid of depressed patients (George et al., *Biol. Psych.* 1994). Furthermore, a first clinical investigation on the effects of PREG in healthy volunteers revealed a general tendency of reduced subjective depression ratings (Meieran et al., *Psychoneuroendocrinology* 2004). Moreover, antidepressant drugs increased PREG levels in rat hippocampus (Serra et al., *Psychopharmacology* 2001), while models of depression such as social isolation decreased it (Serra et al., *J. Neurochem.* 2000). Thus, PREG has been shown as having some beneficial effect in the CNS, both in case of traumatic lesion and in case of depressive disorders.

PREG is a metabolite of cholesterol and the precursor of all steroid hormones. The synthesis of these hormones implies the conversion of the PREG $\Delta 5$-$3\beta$-OH structure to $\Delta 4$-$3$-ketone derivatives (implemented by an enzyme called $3\beta$HED). The Applicant blocked the $\Delta 5$-$3\beta$-OH structure to prevent this metabolic conversion and also to prevent, the formation of the ester sulfate, of PREG, a molecule that can be detrimental at high concentrations. Thus, the Applicant has revealed a compound, 3-methoxy-pregnenolone ($3\beta$-methoxy-pregna-5-ene-20-one, abbreviated as 3-methoxy-PREG), which possesses these properties and which, moreover, is at least as active as PREG in promoting microtubule polymerization and function. It was verified by mass spectrometry coupled with gas chromatography that 3-methoxy-PREG is not converted into PREG.

3-methoxy-PREG is also not converted into PREG metabolites, such as progesterone (PROG) and its further metabolites with progestative activity anon as allopregnanolone or epipregnanolone or pregnenolone sulfate. As a result, 3-methoxy-PREG has no progestative activity and is thus not a progestin. It was further verified that 3-methoxy-PREG does not have any agonist activity on many steroid hormone receptors (see Examples 11 and 13). 3-methoxy-PREG thus has no steroid hormone activity, which may further limit potential adverse effects in vivo.

DESCRIPTION OF THE INVENTION

The Applicant considers as well that the invention is related to 3-methoxy-PREG, but also to all the steroid and steroid-like molecules derived from or mimicking PREG, and in particular molecules derived from PEED, that contain a 3-methoxy function or present a 3β function that can be converted into 3-methyl-ether. These molecules are incapable then of being converted into metabolites endowed with progestative (progesterone is a direct metabolite of PREG and, in addition to its hormonal activity, it is an in vitro PEED antagonist for the polymerization of microtubules), androgenic, estrogenic, glucocorticoid and mineral corticoid activity (see Examples 11 and 13). Also, they cannot be converted into ester sulfates which, such as the sulfate of PREG, can lead to undesired (neurotoxic) side effects.

Within the scope of this invention, the Applicant has revealed the fact that 3-methoxy-PREG, or other molecules according to the invention, can play a major role in the polymerization and/or stabilization of microtubules, and presents quite remarkable activities for the treatment of pathologies related to the nervous system.

By "pathologies related to the nervous system" it is meant pathologies related to the central or peripheral nervous system, particularly those pathologies in which neurocellular microtubules are affected.

3-methoxy-PREG presents the following formula:

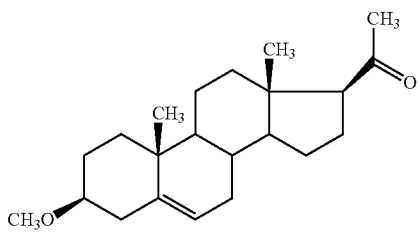

Thus, the invention relates to the use of 3-methoxy-PREG or any molecule derived from pregnenolone or from others 3β-hydroxylated steroids/sterols, incapable of being converted into sulfate esters and/or incapable to be converted by oxidation to hormonally active molecules, for the preparation of a drug intended to stimulate the polymerization, stabilization and function of neuronal microtubules to treat pathologies related to the nervous system particularly acute or chronic lesions or a degenerative disease or depressive disorder with the aforementioned molecule presenting general formula I:

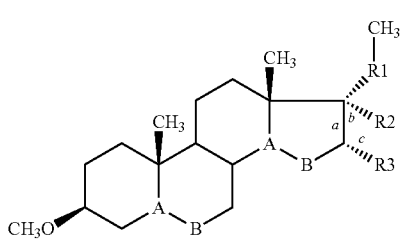

in which

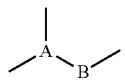

represents

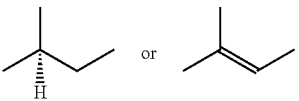

R1=—CO—; CH(OH)— or —CH(O—COCH$_3$)—
R2=H or CHCl$_2$,
R3=H or CH$_3$, or
R2 and R3 together form a ring:

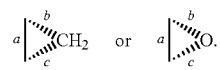

The invention relates to the use of 3-methoxy-PREG or a molecule derived from pregnenolone that contains a 3-methoxy function and is incapable of being converted into a metabolite or ester sulfate of pregnenolone, for the preparation of a drug intended to stimulate the polymerization and/or the stabilization of microtubules to treat an acute or chronic lesion or a degenerative disease or a depressive state of the nervous system with the aforementioned molecule presenting general formula I:

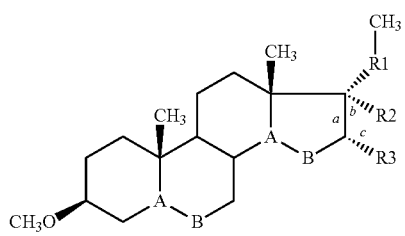

in which:

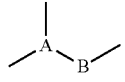

represents

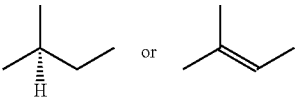

R1=—CO—; —CH(OH)— or —CH(O—COCH$_3$)—
R2=H or CHCl$_2$,
R3=H or CH$_3$, or

R2 and R3 together form a ring:

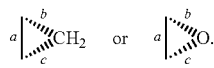

In a preferred embodiment, the aforementioned molecule is 3-methoxy-PREG (3β-methoxy-pregna-5-ene-20-one).

In another embodiment, the aforementioned molecule is 3β-methoxy-pregna-5-ene-20-one-17-α-dichloromethyl.

In another embodiment, the aforementioned molecule is 3β-methoxy-5α-pregnane-20-one.

In another embodiment, the aforementioned molecule is 3β-methoxy-5α-pregnane-20-one.

In another embodiment, the aforementioned molecule is 3β-methoxy-PREG-16α-methyl.

In another embodiment, the aforementioned molecule is 3β-methoxy-PREG-16β-methyl.

In another embodiment, the aforementioned molecule is 3β-methoxy-pregna-5,14-diene-20-one.

In another embodiment, the aforementioned molecule is 3β-methoxy-PREG-16α, 17α-epoxy.

In another embodiment, the aforementioned molecule is 3 methoxy-PREG-16α,17α-methylene.

In another embodiment, the aforementioned molecule is 3β-methoxy-pregna-5-ene-3β,20β-diol-20-acetate.

In another embodiment, the aforementioned molecule is 3β-methoxy-5α-pregnane-20-one-16α-methyl.

3-methoxy-PREG can, within the scope of the present invention, be used to prepare a useful drug to treat other syndromes such as mental slowdown and loss of concentration, pain, including acute pain, post-operative pain, chronic pain, nociceptive pain, neuropathic pain, psychogenic pain syndromes, pain associated with peripheral neuropathies, certain psychiatric states (notably depressive disorders and schizophrenia), dissociative episodes including dissociative amnesia, dissociative fugue and dissociative identity disorder, and other neurodegenerative diseases such as Alzheimer's disease, Parkinson's disease, Huntington's disease, tauopathies, diseases related to prions, amyotrophic lateral sclerosis (ALS), and multiple sclerosis.

In a general way, 3-methoxy-PREG or the molecules derived according to the invention are used to treat any disease in which increased (neuronal) microtubule polymerization and/or stabilization and/or function is sought or is beneficial.

In a preferred embodiment according to the invention, the aforementioned disease is selected from the group comprising Alzheimer's disease, Parkinson's disease, Huntington's disease, tauopathies, age-induced memory loss, age-related dementia, memory loss induced by the taking of substances, a traumatic lesion, in particular a traumatic brain or spinal cord lesion, a cerebral lesion, a lesion of the spinal cord, in particular spinal cord compression, ischemia, pain, notably neuralgia, nerve degeneration, and multiple sclerosis.

In a particularly preferred embodiment, 3-methoxy-PREG or the molecule derived of formula I according to the invention is used to treat a traumatic brain injury.

In another preferred embodiment, 3-methoxy-PREG or the molecule derived of formula I according to the invention is used to treat depressive disorders.

Depression is a mood disorder and can be defined as a mental state characterized by a pessimistic sense of inadequacy and a despondent lack of activity which needs medical treatment due to the high rink of suicide.

The two main types of mood disorders are major (unipolar) depression and bipolar disorder. Major depression is diagnosed following standard clinical criteria such as those recommended by the American Psychiatric Association in the Diagnostic and Statistical Manual of Mental Disorders (DSM-IV). Accordingly, individuals are considered to have an episode of major depression when depressed mood, loss of interest or diminished sense of pleasure have been clearly evident for at least two weeks. Additionally, they have to show five of more of other features nearly every day during the same two week span. These features include large increase or decrease in appetite, insomnia or excessive sleeping, restlessness or slowness of movement, fatigue or loss of energy, feelings of worthlessness or excessive or inappropriate guilt, diminished concentration and decisiveness, suicidal ideation or suicidal attempts.

Episodes may be isolated or recurrent and categorized as mild, moderate or severe based on the intensity of depressive symptoms. In DSM-IV, depression is classified under codes 296.20 to 296.26 for Major depressive disorder, single episode; 296.30 to 296.36 for Major depressive disorder, recurrent; 300.4 for Dysthymic disorder; and 311 for Depressive disorder Not Otherwise Specified.

Common subtypes of major depression include atypical depression, melancholic depression, psychotic depression and geriatric depression. Other subtypes include dysthymia, postpartum depression, post stroke depression, and subcortical ischemic depression.

Atypical depression is characterized by mood reactivity (paradoxical anhedonia) and positivity, significant weight gain or increased appetite, excessive sleep or somnolence (hypersomnia), leaden paralysis, or significant social impairment as a consequence of hypersensitivity to perceived interpersonal rejection. Contrary to its name, atypical depression is between the most common forms of depression.

Melancholic depression is characterized by a loss of pleasure in most or all activities, a failure of reactivity to pleasurable stimuli, severe depressed mood and excessive guilt, a worsening of symptoms in the morning hours, early morning waking, psychomotor retardation, excessive weight loss and decreased appetite.

Psychotic depression is characterized by psychotic (schizophrenic-like) features. These features include hallucinations or delusions that are either mood-congruent (content coincident with depressive themes) or non-mood congruent (content not coincident with depressive themes).

Finally, geriatric depression affects about 5% to 15% of community-dwelling older adults (i.e. adults aged 65 years or more) and is characterized by impairments in cognition (a syndrome sometimes referred as pseudodementia), by psychomotor agitation or retardation, and by high rates of suicide. Clinical major depression can present a combination of these subtypes. For instance someone may experience loss of pleasure in activities as seen in melancholic depression in addition to over-eating and weight gain common to atypical depression.

In a preferred embodiment, 3-methoxy-PREG or the molecules derived of formula I according to the invention, used to treat depressive disorders, are used for treating major or depression, dysthymia, postpartum depression, post stroke depression, and subcortical ischemic depression. Preferably, when major depression is treated, it is selected from the group consisting of atypical depression, melancholic depression, psychotic depression and geriatric depression.

In a preferred embodiment, and notably to treat diseases related to a central nervous system disturbance, the aforementioned drug also comprises an excipient or a compound that makes it possible to formulate the aforementioned 3-methoxy-PREG such that it crosses the blood-brain barrier better. Such an excipient or compound can also make possible a faster or more long-lasting crossing of the aforesaid blood brain barrier.

Such an excipient or compound can be a peptide, such as the peptides described in application WO 00/32236, or 2-pyrrolidone.

The pharmaceutical compositions used in the invention can be administered by any route of administration including, but without being limited to, oral, intravenous, intramuscular, intraarterial, intraspinal, intratechal, intraventricular, transdermal, subcutaneous, intraperitoneal, intranasal, enteral, topical, sublingual, vaginal and rectal.

A continuous or long-term treatment conducted directly via the cerebrospinal fluid using a pump implanted in the subarachnoid specie in the brain or spinal cord can be envisaged. Such an implant could contain a concentrated solution of 3-methoxy-PREG (for example of isopropyl-beta-cyclodextrin diluted with artificial cerebrospinal fluid).

Moreover, 3-methoxy-PREG can be administered with other compounds that contain biologically active agents (for example tensioactives, excipients, transporters, thinners and/or pharmaceutically acceptable vehicles). These compounds are well-known to those skilled in the art. Details on these chemicals can be found in the latest edition of Remington's Pharmaceutical Sciences (Maack Publishing Co., Easton, Pa.).

In the pharmaceutical compositions provided by the present invention for oral, sublingual, subcutaneous, intramuscular, intravenous, transdermal, local, vaginal or rectal administration, the active ingredient (3-methoxy-PREG or a derived molecule) can be administered in unit dose formulations or in mixtures with traditional pharmaceutical media, applicable to animals or humans. Suitable unit dose administration formulations include oral route formulations such as tablets, coated tablets, pills, capsules and soft gelatin capsules, oral powders, granules, solutions and suspensions, sublingual and buccal administration formulations, subcutaneous, intramuscular, intravenous, intranasal, and intraocular administration formulations, and vaginal or rectal administration formulations.

Pharmaceutical compositions can also contain preservatives, agents, stabilizers, wetting agents, emulsifiers, sweeteners, dyes, flavoring, salts intended to modify osmotic pressure, buffers, taste correctors, and antioxidants. They can also contain other therapeutically active substances.

Thus, pharmaceutical compositions according to the invention can also contain other steroids known to exert pro-cognitive effects. Additionally, neuroprotective and neuro-stimulant agents can also be included in the pharmaceutical composition, notably compounds which increase neuronal regeneration. Such agents can be selected in particular from among the neuronal growth factors such as fibroblast growth factors (FGFs), acidic or basic, FGF-3, FGF-4, FGF-6, or keratinocyte growth factor (KGF). The addition of a neuroprotective agent can be envisaged, such as nerve growth factor (NGF), brain derived neurotrophic factor (BDNF), neurotrophin 3 or 4, TGF-beta 0.1, interleukins, or insulin-like growth factors (IGFs). Finally, the addition of peptides known to bind other microtubular components such as the activity-dependent neuroprotective protein (ADNP) and the ADNP-related peptide NAP, which bind the neuronal βIII-tubulin, can be also considered due to their promoting effect on microtubule polymerization and function and their neuroprotective properties (Gozes et al., *CNS Drug Rev.* 2005).

Any other types of therapeutic antioxidant or neuroprotective agents can be used, notably glutamate inhibitors.

When a solid composition in tablet form is prepared, the principal active ingredient is mixed with a pharmaceutical vehicle such as gelatin, starch, lactose, stearic acid or magnesium stearate, talc, gum arabic or analogues. The tablets can be coated with saccharose or other suitable materials or even be treated so as to have a prolonged or delayed activity and to release continuously a predetermined quantity of the active ingredient.

A capsule preparation is obtained by mixing the active ingredient with a thinner and pouring the mixture obtained into soft or hard capsules, with excipients such as vegetable oils, waxes, fats, semi-solid or liquid polyols, etc.

A preparation in syrup or elixir form can contain the active ingredient together with a sweetener, an antiseptic, as well as an agent giving taste and a suitable dye. Excipients can be used such as water, polyols, saccharose, invert sugar, glucose, etc.

Powders or water-dispersible granules can contain the active ingredient in a mixture with dispersing agents, wetting agents, and suspending agents, together with taste correctors and sweeteners.

Suppositories, which are prepared with binders that melt at rectal temperatures, for example cocoa butter or semi-solid or liquid polyols such as polyethylene glycols, waxes, natural or hydrogenated oils, fats, etc., can be used for vaginal or rectal administration.

For parenteral, intranasal, or intraocular administration, aqueous suspensions, isotonic saline solutions, or sterile, injectable solutions that contain pharmacologically compatible dispersing agents and/or wetting agents can be used. As an excipient, water, alcohols, polyols, glycerol, vegetable oils, etc., can be used.

The active ingredient can also be formulated in the form of microcapsules, possibly with one or more additive supports.

For the treatment of pain, topical application is the preferred route of administration. Here, the compositions according to the invention can be presented in the form of a gel, a paste, an ointment, a cream, a lotion, an aqueous or aqueous-alcohol liquid suspension, an oily solution, a dispersion of the lotion or serum type, an anhydrous or lipophilic gel, an emulsion with a liquid or semi-solid milk-type consistency obtained by dispersing a fatty phase in an aqueous phase or vice versa, suspensions or emulsions of a soft or semi-solid cream- or gel-type consistency, or alternatively microemulsions, microcapsules, microparticles, or vesicular dispersions of the ionic and/or nonionic type. These compositions are prepared according to standard methods.

Moreover, a tensioactive can be included in the composition in order to enable deeper penetration by 3-methoxy-PREG.

Among the ingredients envisaged, the invention comprises agents enabling an increase in penetration selected, for example, from the group comprising mineral oil, ethanol, triacetin, glycerin and propylene glycol; cohesion agents are selected, for example, from the group comprising polyisobutylene, polyvinyl acetate, polyvinyl alcohol, and thickening agents.

Thus, in a preferred embodiment according to the invention, the aforementioned drug is presented in an injectable form.

In another preferred embodiment according to the invention, the aforementioned drug is presented in a form allowing oral administration.

Preferably, the aforementioned drug comprises an effective quantity of 3-methoxy-PREG, in particular ranging between 25 and 2500 mg or between 50 and 2500 mg, preferably between 25 and 250 mg, and by the parenteral route.

The aforementioned drug comprises preferentially an effective quantity of 3-methoxy-PREG or any molecule derived from pregnenolone or from 3β-hydroxylated steroids/sterols, incapable of being converted into sulfate esters and/or incapable to be converted by oxidation to hormonally active molecules, preferably 3-methoxy-PREG or a molecule derived from pregnenolone that presents a 3-methoxy function, such that the quantity administered to the patient is comprised between 0.1 and 100 mg/kg body weight, preferably between 1 and 100 mg/kg body weight, or between 0.1 and 10 mg/kg body weight.

An effective quantity of 3-methoxy-PREG is a quantity which allows, within the meaning of the present invention, the stabilization and/or polymerization of microtubules after administration to the host. Thus, the administration of an effective quantity of 3-methoxy-PREG results in the retardation, the improvement or the elimination of the disease. The quantity of 3-methoxy-PREG administered to the host will, vary as a function of factors which include the height, age, weight, general health, sex, and diet of the host, the time of the administration, and the duration and characteristics of the disease associated with microtubule depolymerization/destabilization. The adjustment of dosages is well-known to those skilled in the art.

Thus, the invention relates to a therapeutic use of 3-methoxy-PREG. Thus, the invention relates to this compound as a drug.

A pharmaceutical composition comprising as an active ingredient 3-methoxy-PREG or any molecule derived from pregnenolone or from others 3β-hydroxylated steroids/sterols, incapable of being converted into sulfate esters and/or incapable to be converted by oxidation to hormonally active molecules, preferably 3-methoxy-PREG or a compound derived from pregnenolone having a 3-methoxy function of, general formula I, and a pharmaceutically acceptable excipient, is also an object of the invention.

The Applicant has revealed the activity of 3-methoxy-PREG which stabilizes and/or induces microtubule polymerization in a cell.

Thus, in a more general way, the invention relates to a method for increasing the stabilization and/or inducing the polymerization of the microtubules in a cell, comprising the step of exposing the aforementioned cell to the presence of 3 methoxy at a concentration from approximately 0.1 to 100 μM or 0.5 to 100 μM, preferably 0.1 to 50 μM or 0.5 to 50 μM. Microtubule polymerization can be analyzed by immunolabeling the MAP2 protein associated with these microtubules. Preferably, this method is implemented in, vitro, but can be implemented in vivo, or ax vivo (on cells isolated from a patient, treated in vitro and re-injected) in certain cases.

The invention also relates to a method for increasing the growth of neurites in a cell, comprising the step of exposing the aforementioned cell to the presence of 3-methoxy-PREG at a concentration from approximately 0.5 to 50 μM. This method is also implemented in vitro by preference, without excluding other modes of implementation if necessary.

The invention also relates to a method for promoting neurites branching in, neuronal cells, comprising the step of exposing the aforementioned cell to the presence of 3-methoxy-PREG at a concentration from approximately 0.1 to 50 μM. This method is also implemented in vitro by preference, without excluding other ways of implementation if necessary.

The invention has also as an aim a method for reducing the depolymerization of microtubules and/or the retraction of neurites in a cell, comprising the step of exposing the aforementioned cell to the presence of 3-methoxy-PREG at a concentration from approximately 0.5 to 50 μM. This method is implemented in vitro also by preference, without excluding other modes of implementation if necessary.

The invention has also as an aim a method for reducing the depolymerization of microtubules and/or recovering the extension of neurites in a cell, comprising the step of exposing the aforementioned cell to the presence of 3-methoxy-PREG at a concentration from approximately 0.1 to 50 μM. This method is implemented in vitro also by preference, without excluding other ways of implementation if necessary.

The invention also relates to a method for the treatment and/or the prevention of a disease induced or accompanied by the depolymerization of microtubules in a patient, comprising the step of the administration of an effective quantity of 3-methoxy-PREG to the aforementioned patient. As mentioned before, the invention is related to 3-methoxy-PREG or any molecule derived from pregnenolone or from 3β-hydroxylated steroids/sterols, incapable of being converted into sulfate esters and/or incapable to be converted by oxidation to hormonally active molecules. Preferably, the invention relates to 3-methoxy-PREG, but also to all the molecules derived from pregnenolone that contain a 3-methoxy function or present a 3' function that can be converted into 3-methyl-ether and is incapable of being converted into a metabolite or ester sulfate of pregnenolone, said molecule being of formula I.

In a particular embodiment, the invention thus relates to a method for the treatment and/or the prevention of a disease induced or accompanied by the depolymerization of microtubules in a patient, comprising the step of the administration to said patient of an effective quantity of 3-methoxy-PREG or any molecule derived from pregnenolone or from others 3β-hydroxylated steroids/sterols, incapable of being converted into sulfate esters and/or incapable to be converted by oxidation to hormonally active molecules, preferably of 3-methoxy-PREG or a molecule derived from pregnenolone that contains to 3-methoxy function and is incapable of being converted into a metabolite or ester sulfate of pregnenolone of formula I, wherein said disease is a depressive disorder. In a preferred embodiment, said depressive disorder is selected from the group consisting of major depression, dysthymia, postpartum depression, post stroke depression, and subcortical ischemic depression. More particularly, when major depression is treated, major depression is advantageously selected from the group consisting of atypical depression, melancholic depression and psychotic depression.

In such methods according to the invention, any molecule of formula I, any excipient, any administration route, or any dosage mentioned above may be used.

The invention also relates to a method for the treatment and/or the prevention of a neurodegenerative disease or lesion in a patient, comprising the step of the administration of an effective quantity of 3-methoxy-PREG to the aforementioned patient.

A method to treat a patient after spinal cord compression or trauma, comprising the step of the administration of an effective quantity of 3-methoxy-PREG to the aforementioned patient, is also an object of the invention.

Finally, a method to treat a patient after spinal cord or brain compression or trauma, comprising the step of the administration of an effective quantity of 3-methoxy-PREG to the aforementioned patient, is also an object of the invention.

Mean±SEM, n=7 per group. ***$p<0.001$ vs grouped sesame oil (T-test).

Figure 15:
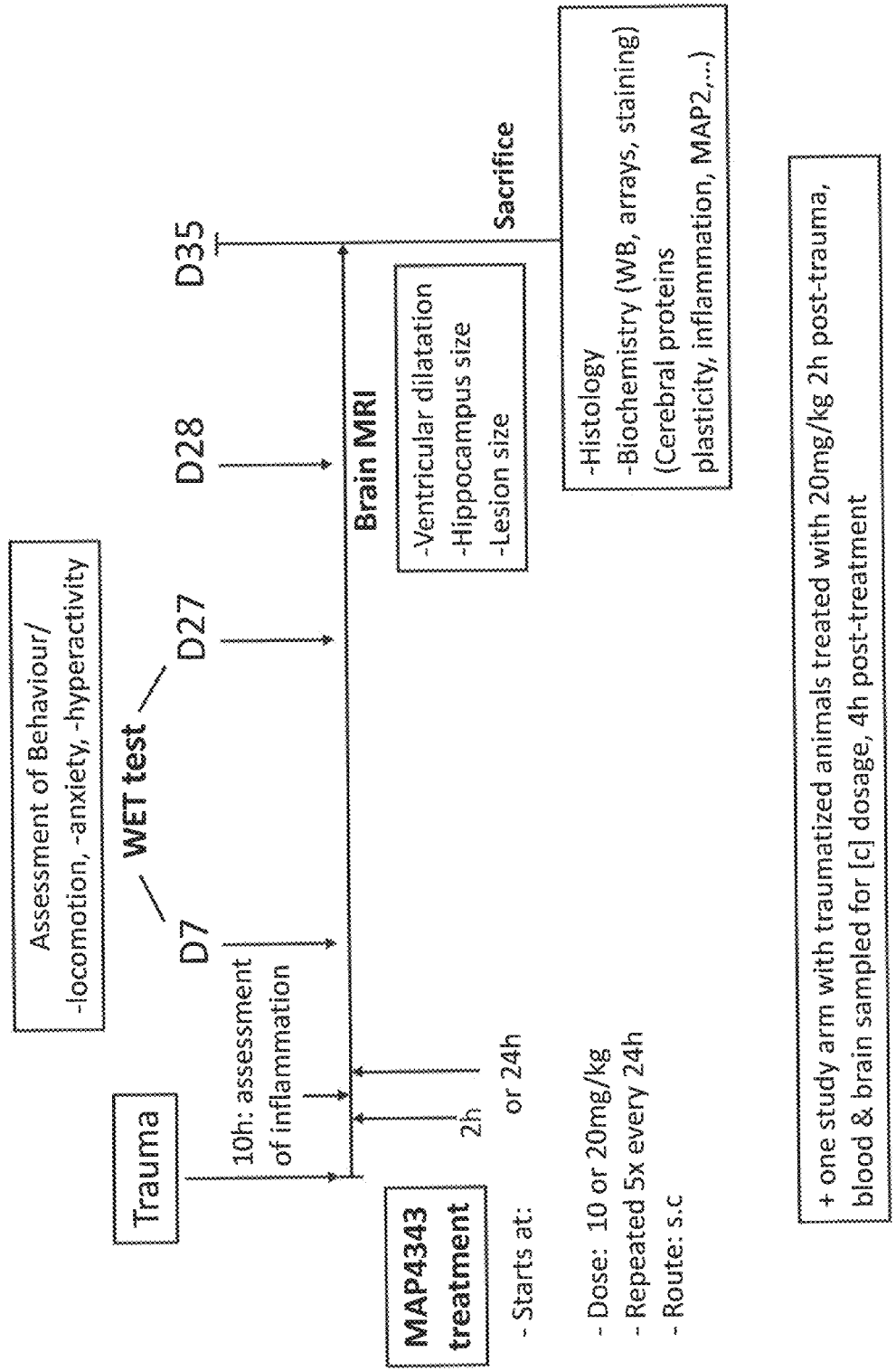

FIG. 15: Overview of the experimental set up used for studying the effect of 3-methoxy-PREG after traumatic brain injury (TBI).

Figure 16:
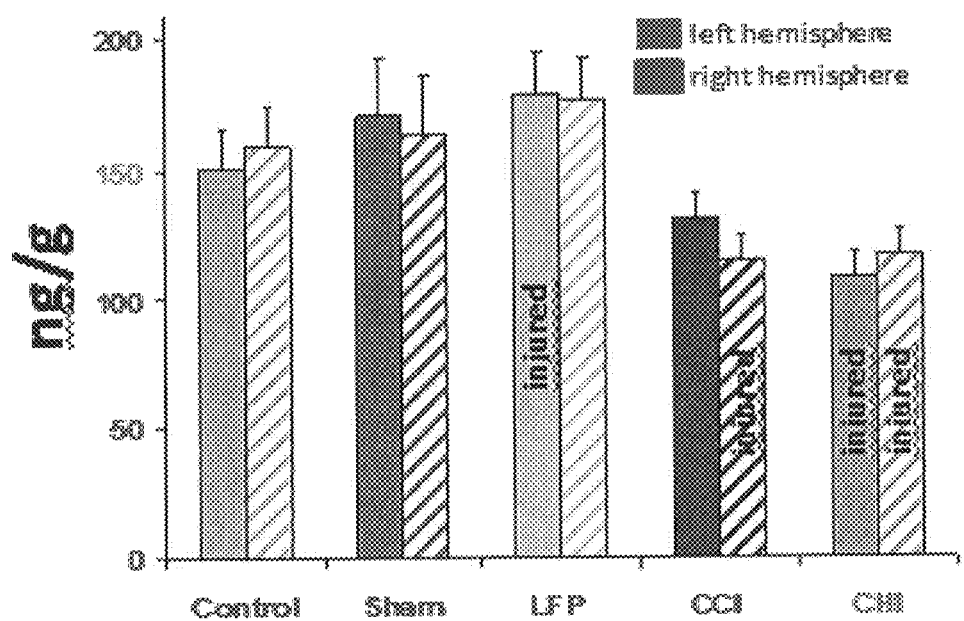

FIG. 16: Concentrations of NAP4343 that reach the brain of treated rats in three trauma models.

Figure 17:
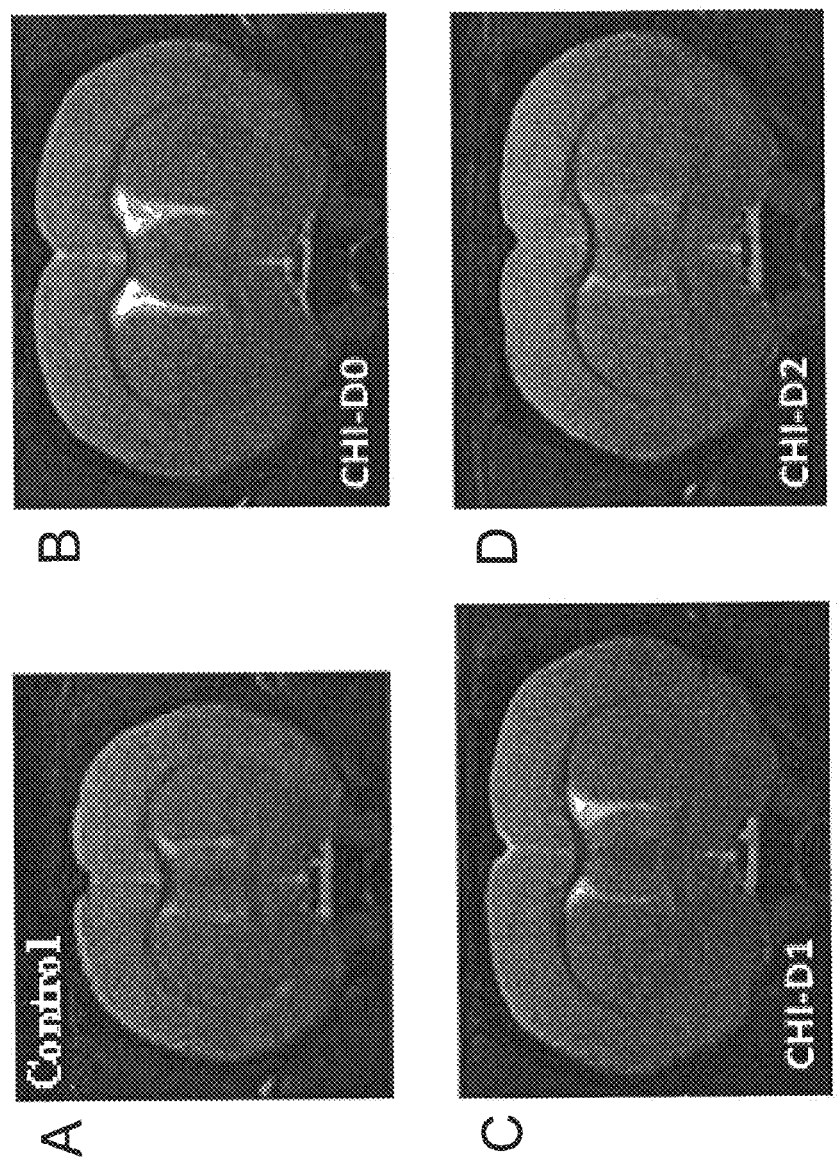

FIG. 17: 3-methoxy-PREG reduces ventricular dilation induced by trauma. (A) Images showing that CHI induces significant ventricular dilatation at day 28 post-trauma. (B) Ventricle areas of CHI traumatized animals injected with sesame oil, NAP4343, or CHI-D2.

Figure 18:
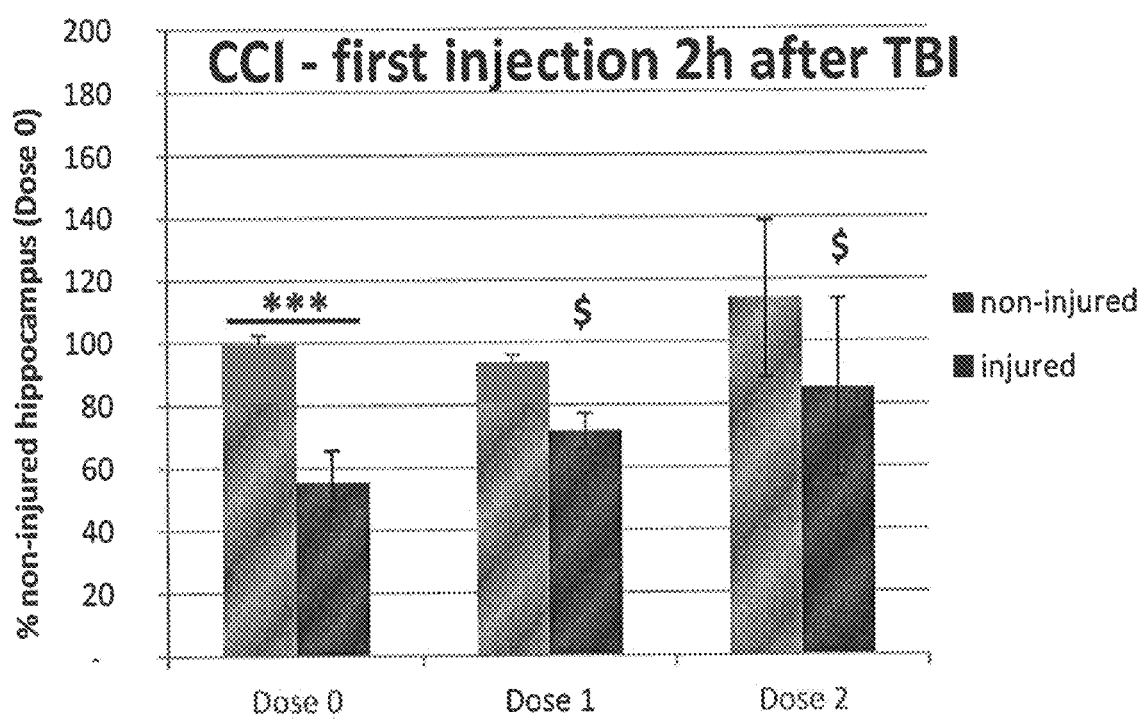

FIG. 18: Effects of 3-methoxy-PREG on the hippocampus size integrity from the lesion induced by trauma.

Figure 19A:
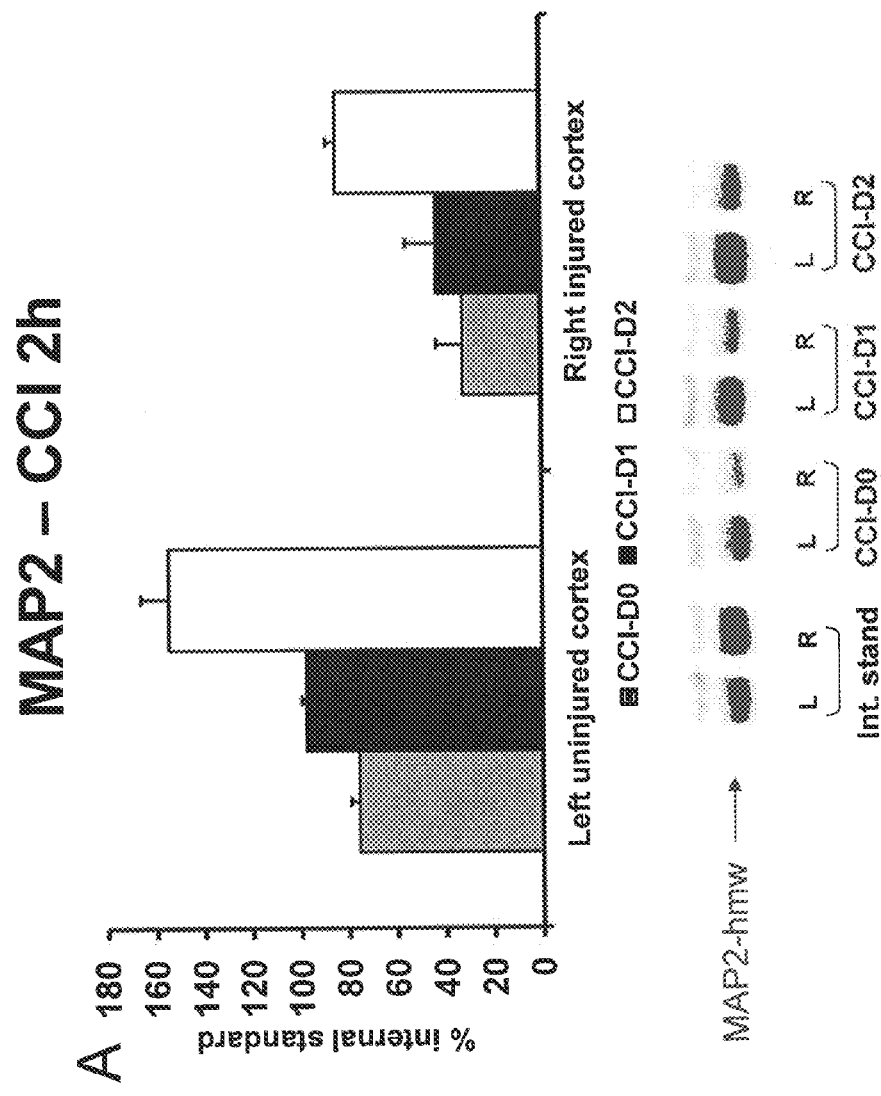
Figure 19B:
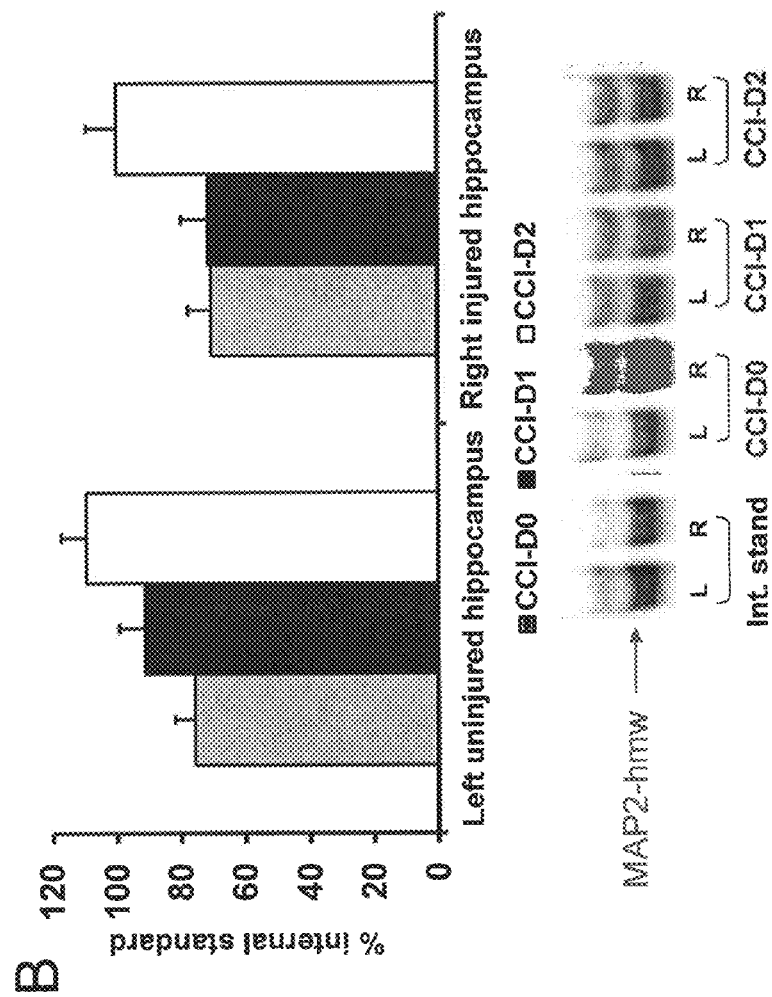

FIG. 19: 3-methoxy-PREG up regulates neuronal brain markers of plasticity. (A) Effects in injured cortex compared to uninjured cortex. (B) Effects in uninjured compared to injured hippocampus. NAP2 is the target of NAP4343 and a modulator of microtubule function.

Figure 20A:
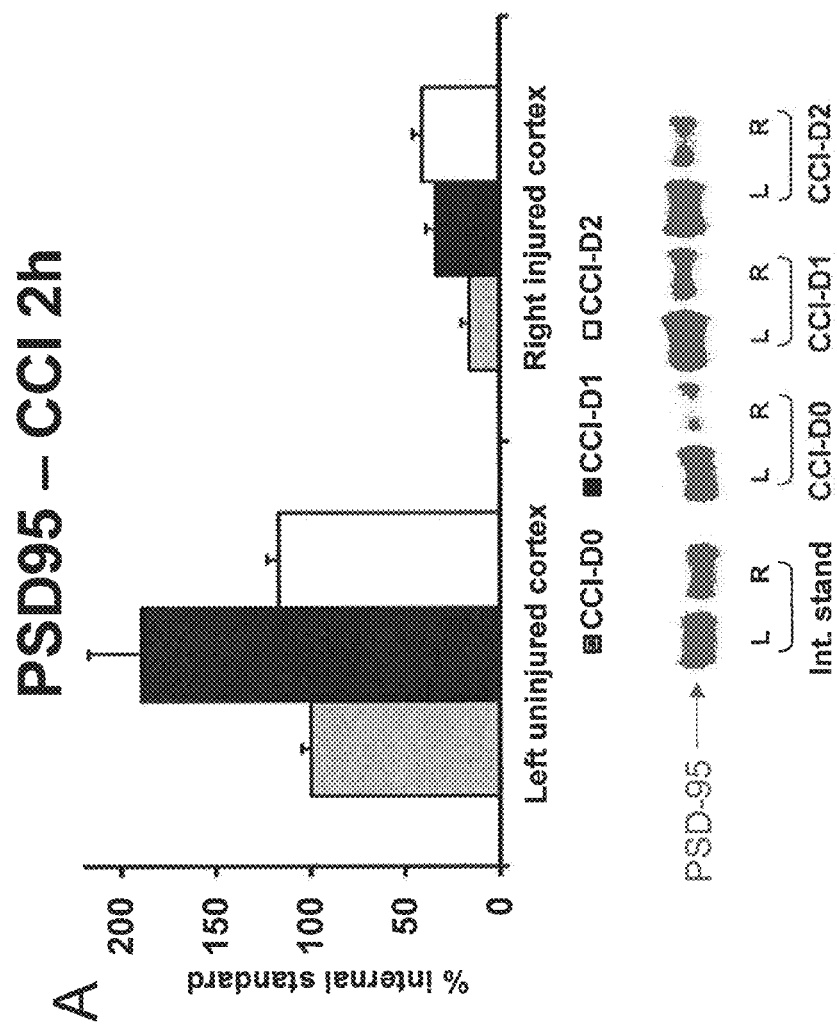
Figure 20B:
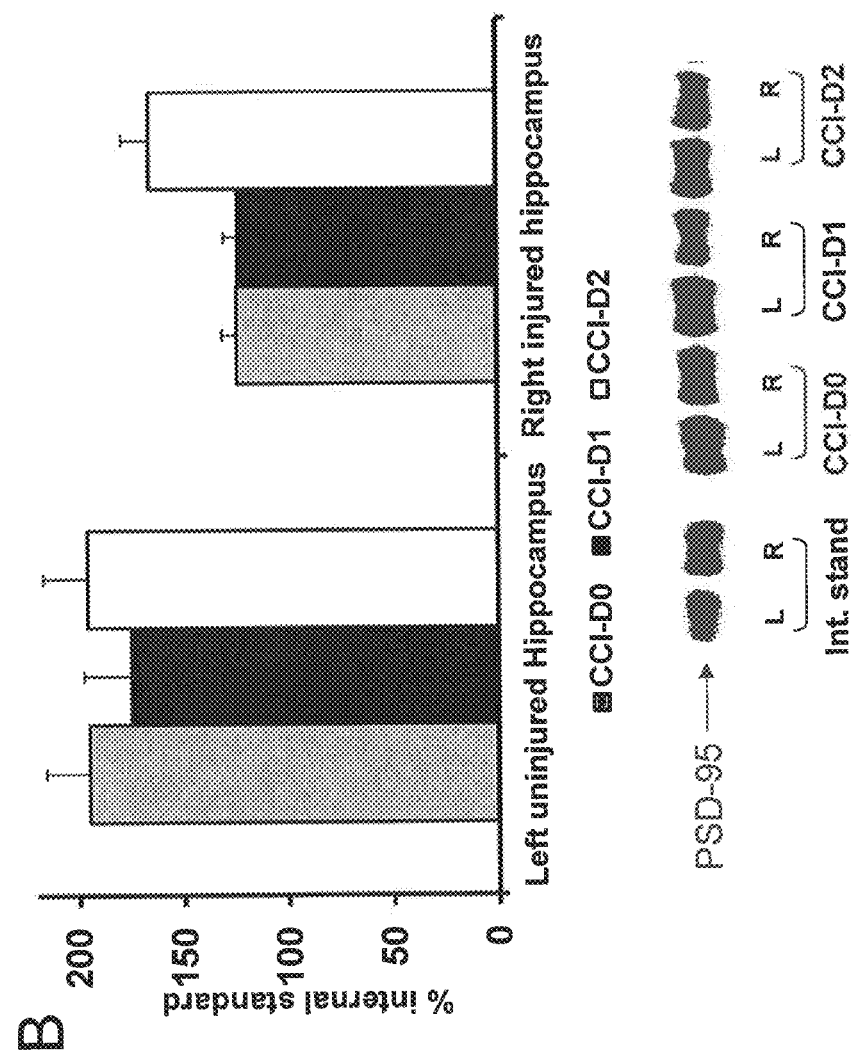

FIG. 20: 3-methoxy-PREG up regulates neuronal brain markers of plasticity. (A) Effects in injured cortex compared to uninjured cortex, (B) Effects in uninjured compared to injured hippocampus. NAP2 is the target of NAP4343 and a modulator of microtubule function. PSD95 is a post synaptic protein.

Figure 21A:
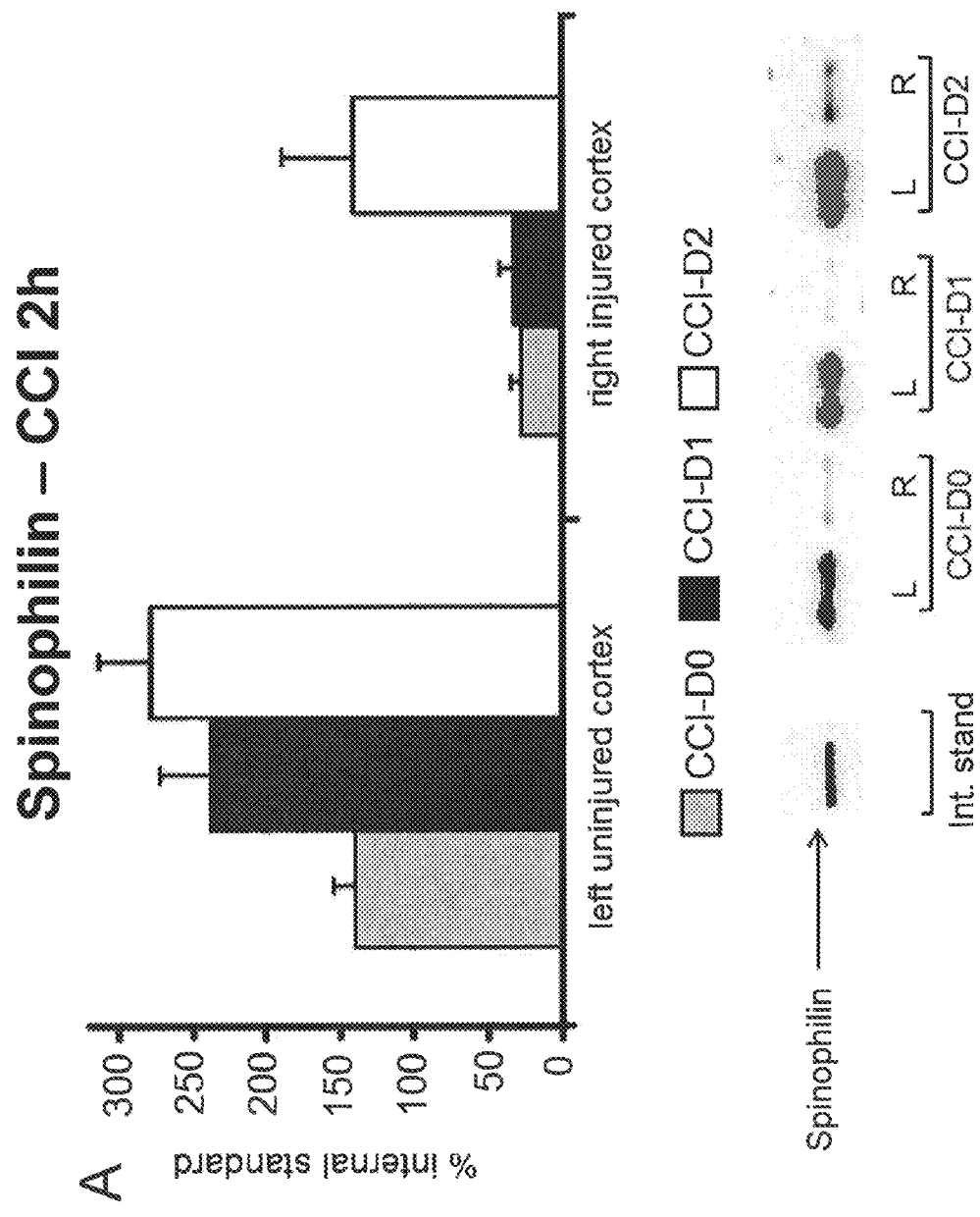
Figure 21B:
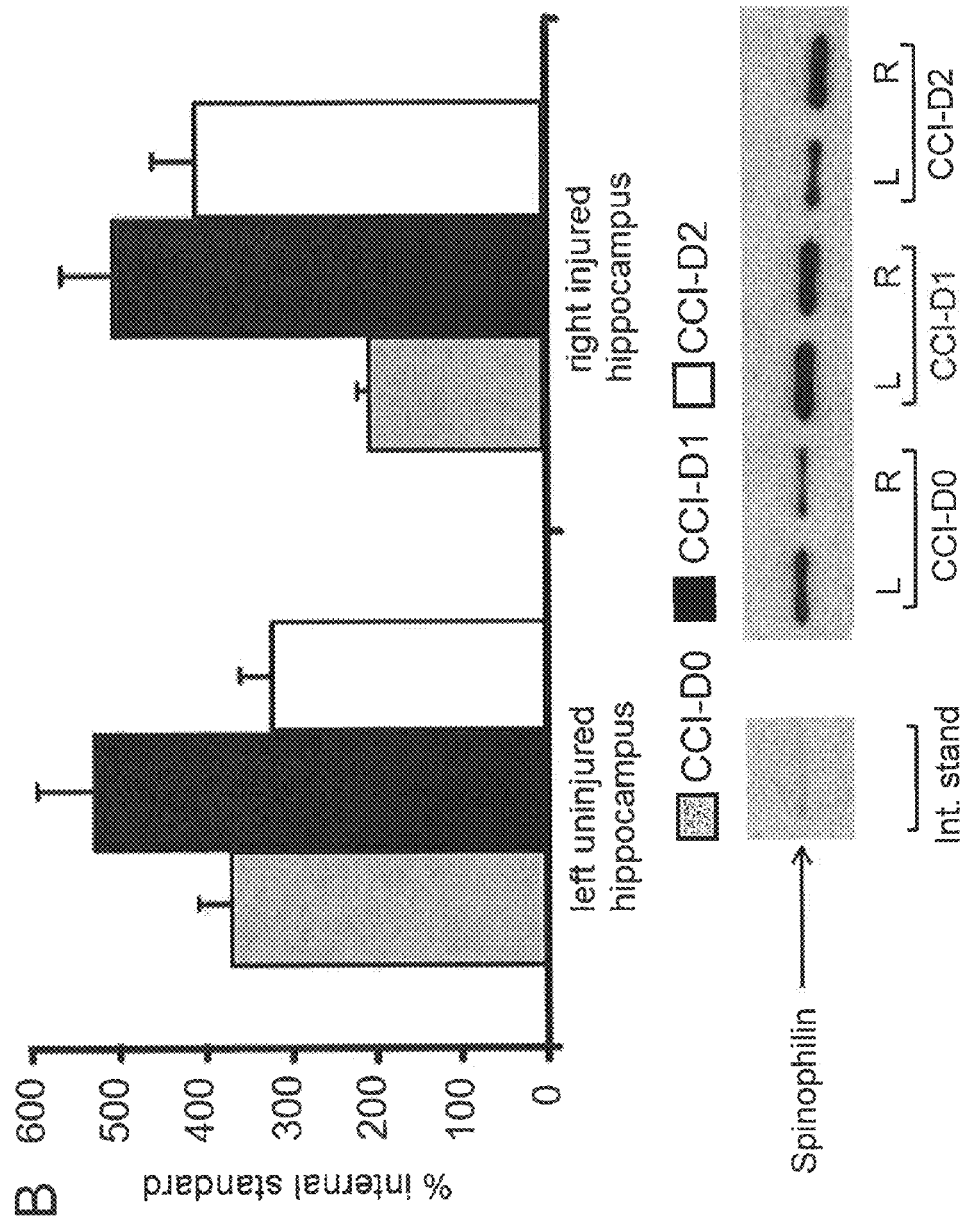

FIG. 21: 3-methoxy-PREG up regulates neuronal brain markers of plasticity. (A) Effects in injured cortex compared to uninjured cortex. (B) Effects in uninjured compared to injured hippocampus. NAP2 is the target of NAP4343 and a modulator of microtubule function. PSD95 is a post synaptic protein. Spinophilin is a post-synaptic protein.

Figure 22A:
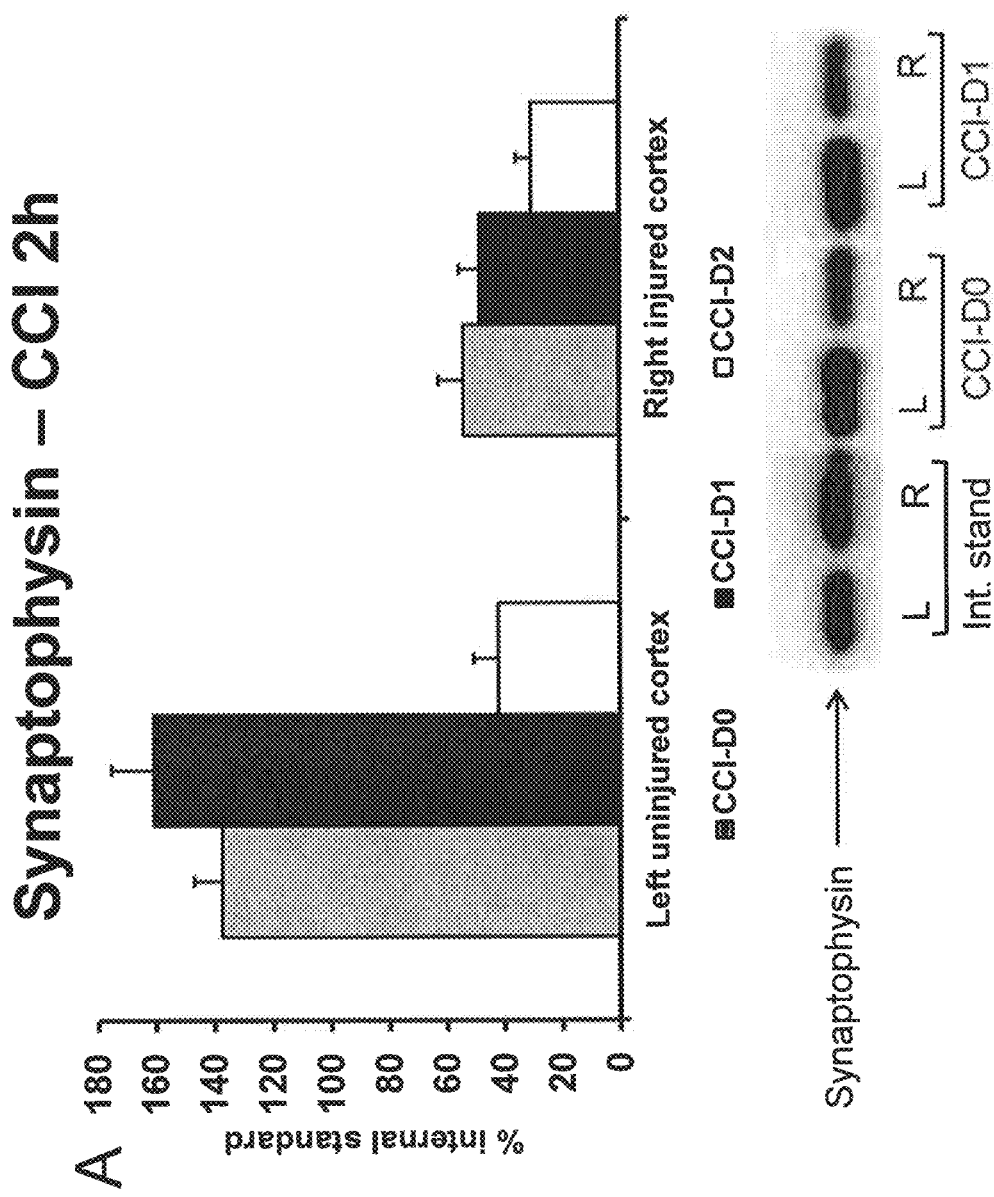
Figure 22B:
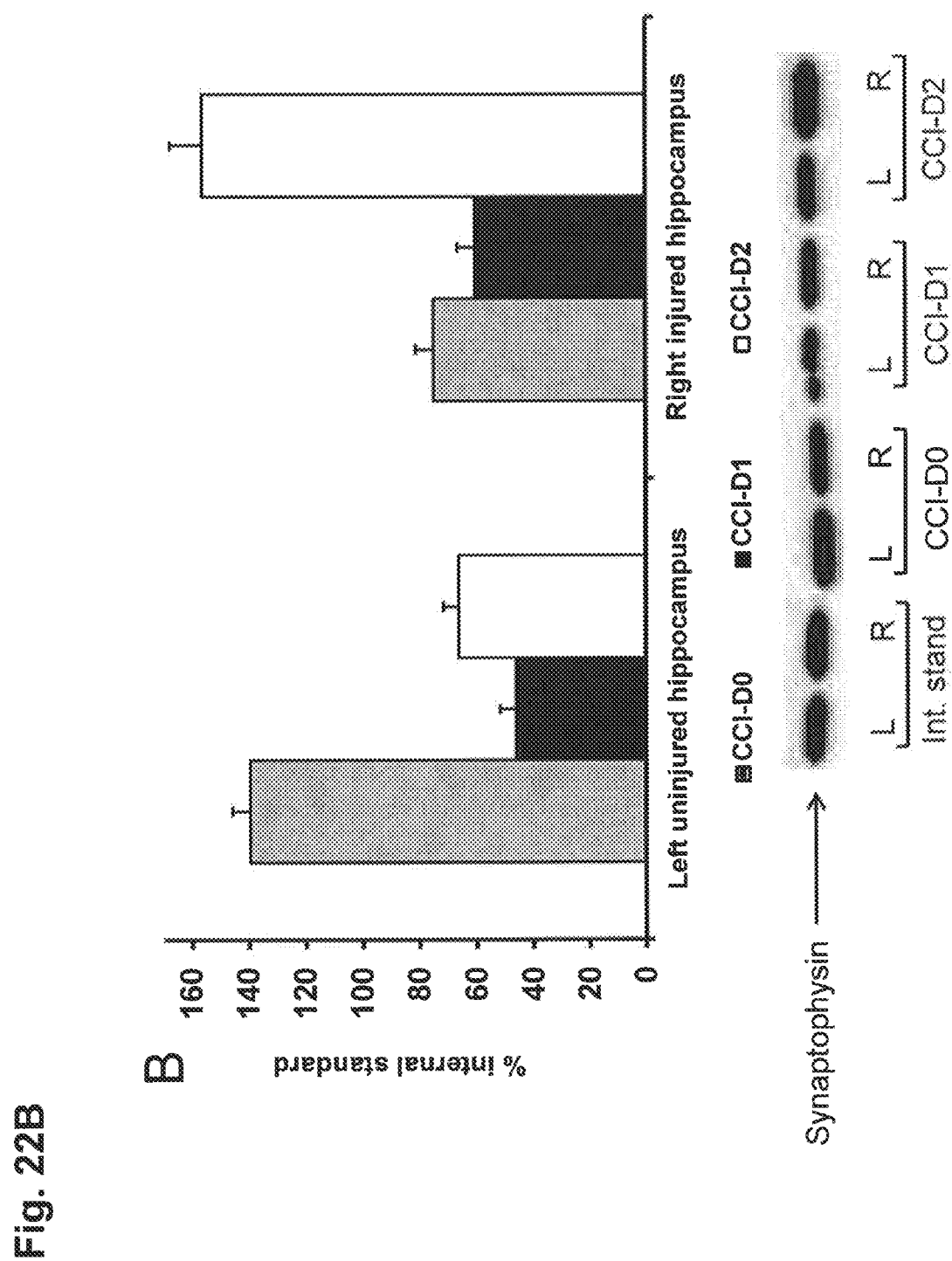

FIG. 22: 3-methoxy-PREG up regulates neuronal brain markers of plasticity. (A) Effects in injured cortex compared to uninjured cortex. (B) Effects in uninjured compared to injured hippocampus. NAP2 is the target of NAP4343 and a modulator of microtubule function. PSD95 is a post synaptic protein. Spinophilin is a post-synaptic protein. Synaptophysin is a pre-synaptic protein.

Figure 23A:
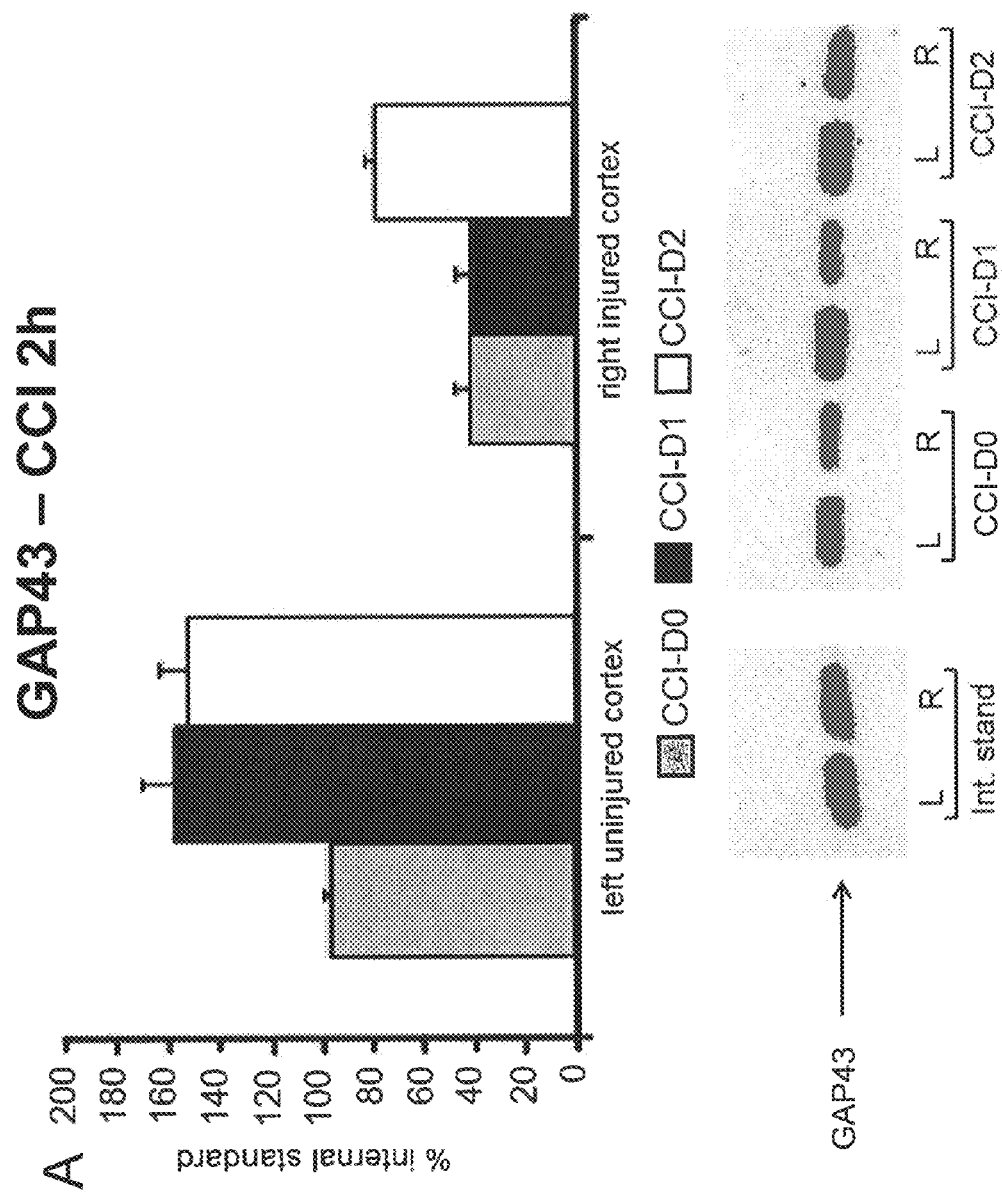
Figure 23B:
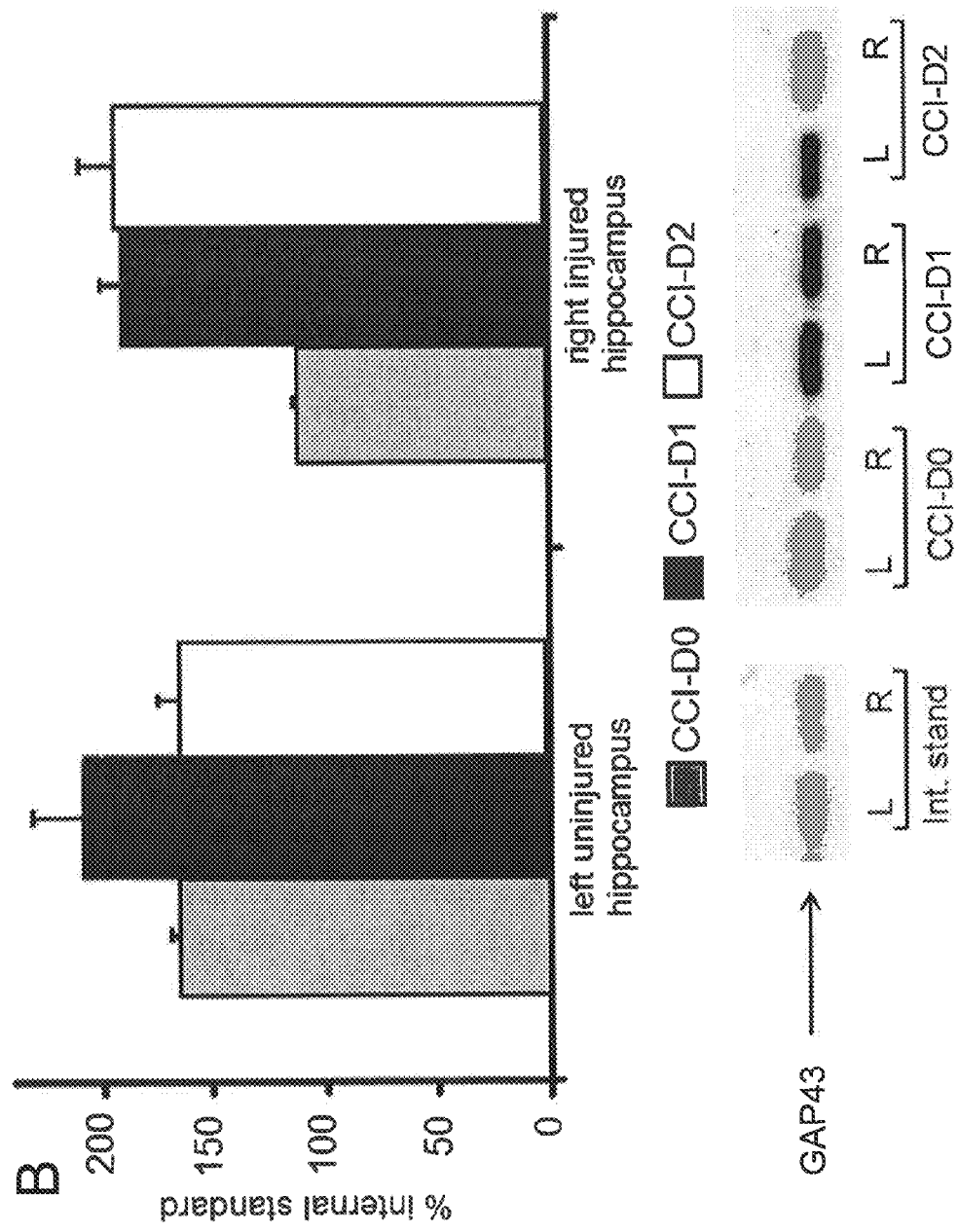

FIG. 23: 3-methoxy-PREG up regulates neuronal brain markers of plasticity. (A) Effects in injured cortex compared to uninjured cortex. (B) Effects in uninjured compared to injured hippocampus. NAP2 is the target of NAP4343 and a modulator of microtubule function. PSD95 is a post synaptic protein. Spinophilin is a post-synaptic protein. Synaptophysin is a pre-synaptic protein. GAP43 is an axonal growth/integrity protein.

Figure 24:
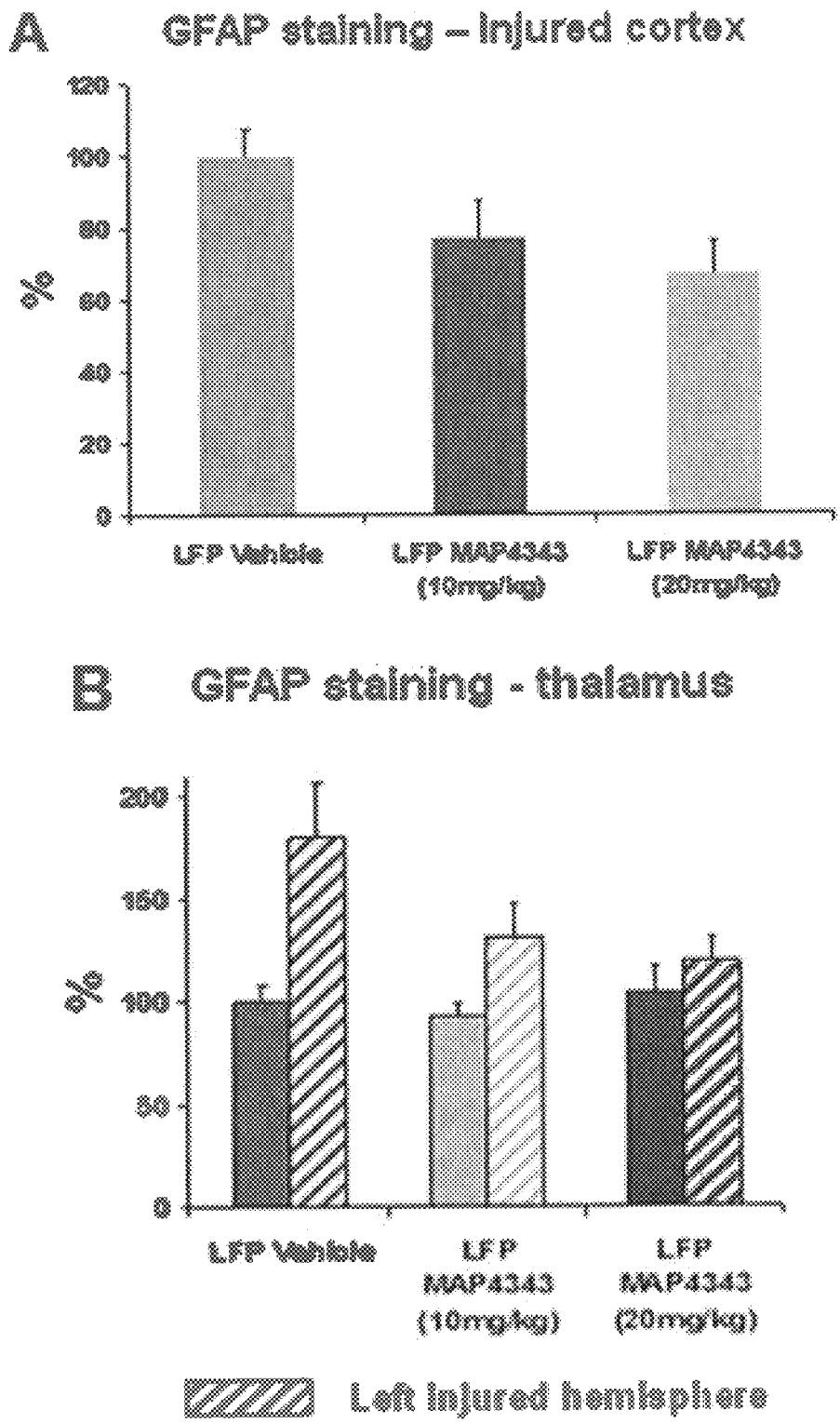

FIG. 24: Results obtained in animals treated with MAP4343. (A) cortex. (B) thalamus.

The examples which follow are intended to illustrate the invention.

EXAMPLES

Example 1

Synthesis of 3-methoxy-PREG (43B)

10 g (52 mmol) of p-toluenesulfonyl chloride is added to a solution of 5 g (15.8 mmol) of pregnenolone in 30 ml of pyridine. The mixture is stirred for 14 hours and then added to 100 ml of distilled water. After cooling the reaction medium to 0° C., the mixture is filtered and the white solid obtained is dried under vacuum to yield 7.4 g (98%) of pregnenolone tosylate.

The 7.4 g of pregnenolone tosylate is refluxed with methanol (50 ml) for 4 hours. After cooling and evaporation of the solvent, the crude reaction product is taken up in 100 ml of ethyl and washed 3 times with 100 ml of a 10% sodium bicarbonate solution. After drying the organic phase over $Na_2SO_4$, it is evaporated dry under reduced pressure to yield 5.2 g (100%) of 3-methoxy-PREG in the form of a white powder.

A novel, synthesis of 3-methoxy-PREG was performed on a kilogram scale. The purity of the end product was confirmed by NMR and was greater than 97.5% with only one minor contaminant easily separable by HPLC. Pregnenolone can be obtained at low cost from commercial sources.

Example 2

Test of 3-Methoxy-PREG (43B) Activity; Comparison with Pregnenolone (PREG)

Figure 1:
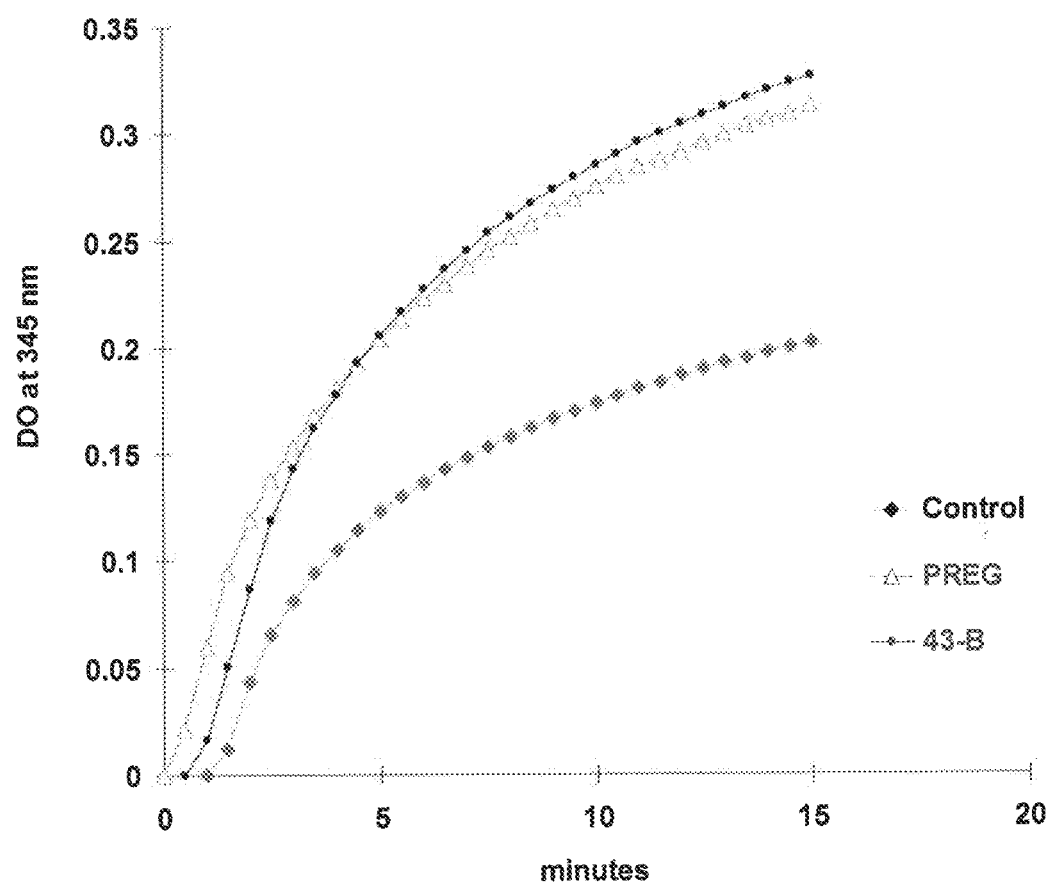
FIG. 1: Kinetics of microtubule polymerization in vitro: effects of PREG (pregnenolone) and molecule 43B (3-methoxy-PREG) both at a concentration of 40 µM. Purified MAP2 and tubulin are mixed in the presence of GTP at 4° C. in a spectrophotometer cuvette. Polymerization is induced by heating at 37° C. and is followed by the increase in optical density (OD) which indicates the quantity of polymers formed. Lag time is decreased in the presence of PREG and molecule 43B, whereas the polymerization rate and the quantity of microtubules clearly increase compared to the control kinetics in the presence of solvent alone.

This in vitro test measures the effect of molecules on the MAP2-induced polymerization of microtubules. This polymerization occurs when MAP2 proteins and tubulin are mixed at adequate concentrations in the presence of GTP. It is accompanied by an increase in optical density measured at 345 nm for 15 to 30 minutes with a UNICON spectrophotometer thermostated at 37° C. (FIG. 1).

It is observed that molecule 43B, corresponding to 3-methoxy-PREG, activates microtubule polymerization as does pregnenolone (PREG). Other molecules, such as progesterone and pregnenolone sulfate, are PREG antagonists and do not stimulate polymerization (not shown).

Example 3

Cellular Models

Effect of Molecules on Neuritic Growth

Figure 2:
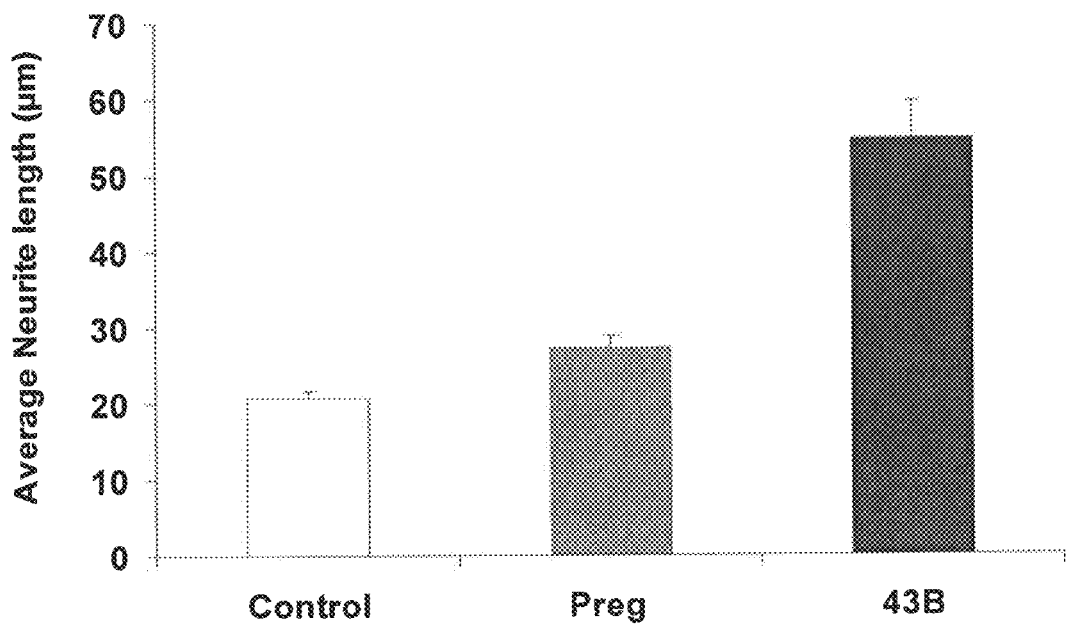
FIG. 2: Effect of PREG and 3-methoxy-PREG (43B) on the average length of neurites in PC12 cells, PC12 cells were cultured for 3 days in the presence of NGF (10 ng/ml) with or without (control) the addition of PREG or 43B molecules (30 µM). Each molecule was tested in three culture wells. Measurements were taken for 200 cells per well using Scion Image software.
Figure 3:
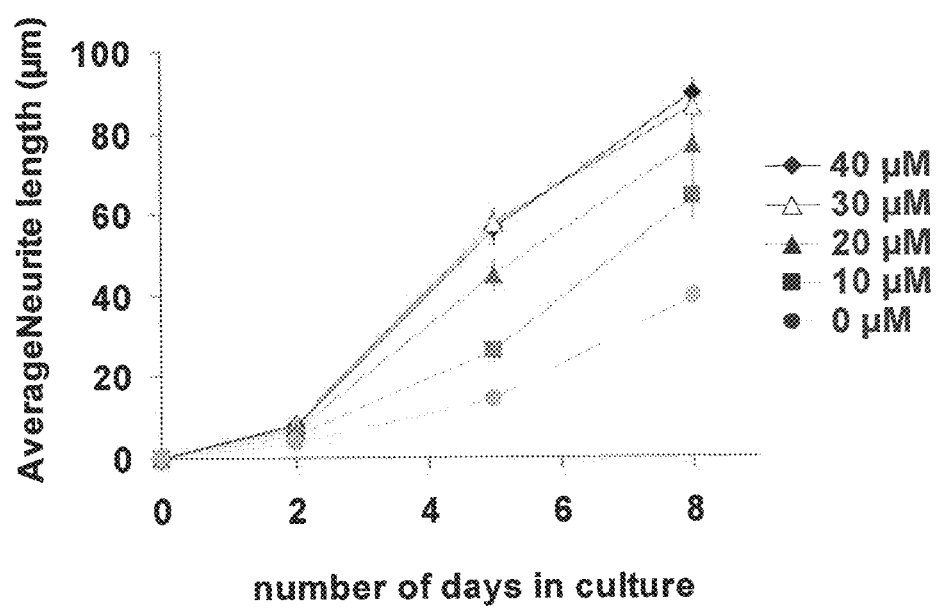
FIG. 3: Dose-response relationship of molecule 43B on the average length of neurites (neurites) in PC12 cells, PC12 cells were cultured in the presence of NGF (10 ng/ml) and increasing concentrations of 3-methoxy-PREG (43B). Neurite (neurite) length was measured for 200 cells per well after 2, 5, and 8 days of culture.
Figure 4:
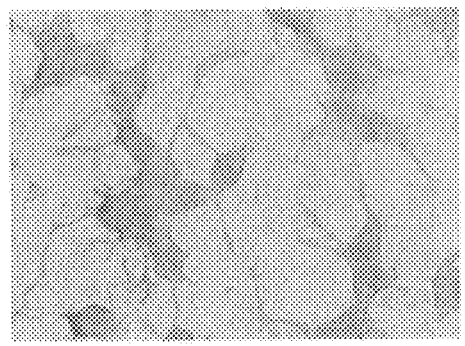
FIG. 4: Immunolabeling of microtubule-associated MAP2 in PC12 cells treated with PREG or 3-methoxy-PREG. PC12 cells were cultured in the presence of NGF (10 ng/ml) and PREG or 3-methoxy-PREG (20 µM). They were fixed and exposed to anti-MAP2 antibodies that reveal microtubule-associated MAP2 esclusively.
Figure 4:
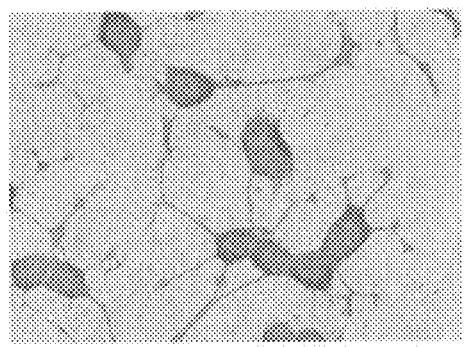
Figure 4:
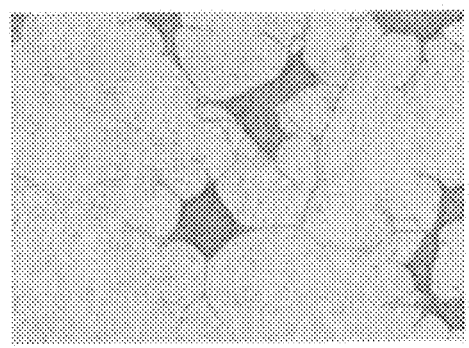

To rest the effect of selected molecules on neuritic growth, we first used the PC12 line, which has long been employed in neurobiological research. In the presence of NOF (nerve growth factor), the cells of this line, which arise from a rat pheochromocytoma, form neuritic extensions containing MAP-associated microtubules. The growth of these elongations is stimulated by the addition of PREG. In the presence of PREG (30 μM), the increase in the average length of the neurites after 3 days of culture reaches 60%. The screening of other natural or synthetic steroids made it possible to select several molecules presenting greater effects than that of PRIG (FIG. 2). In particular, the addition of molecule 43B, which can be synthesized easily from PRIG, caused a spectacular increase (reaching as high as 500%) in the length of neurites formed in the presence of NOF (FIG. 3). This neurite growth accompanies the stimulation by 43-3 of the association of MAP2 to the microtubules (FIG. 4).

Effect of Steroids on the Resistance of Microtabules to Nocodazole

Figure 5:
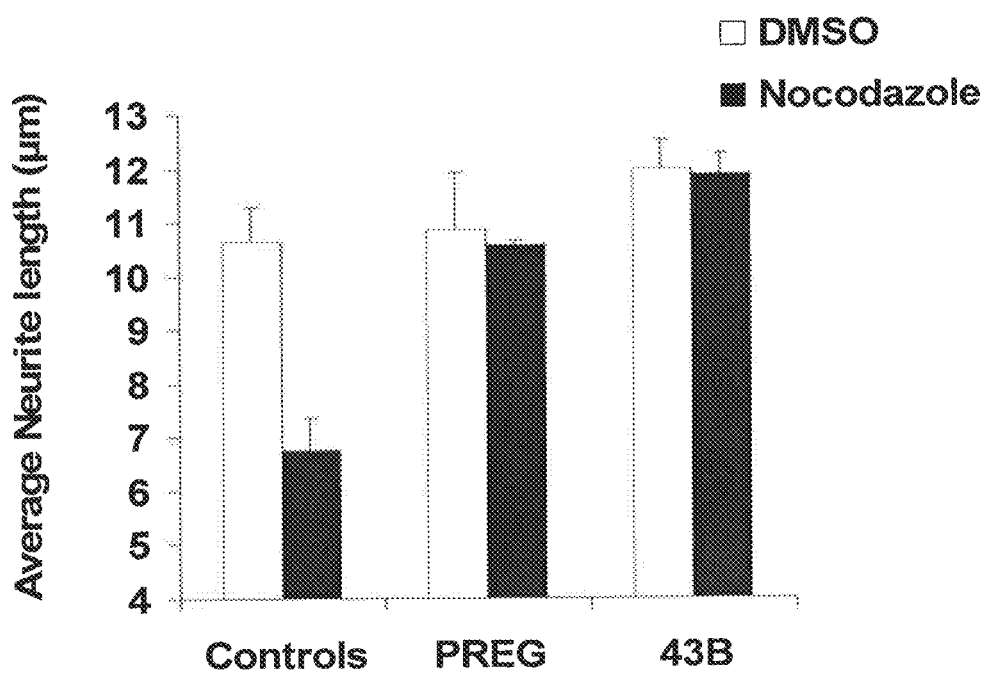
FIG. 5: Retraction of neurites (neurites) induced by nocodazole. After 7 days of culture in the presence of NOF (10 ng/ml), the cells were pretreated for one hour with PREG (30 µM) or 43B (30 µM), then exposed to nocodazole for 15 minutes (white columns: DMSO solvent alone; gray columns: nocodazole).

Nocodazole is a microtubule depolymerizing agent. Its addition to PC12 cell cultures, differentiated in the presence of NGF, causes neurites to retract as a result, of the depolymerization of their microtubules. Pretreatment of the cells by PREG or 43B makes the neurites resistant to nocodazole due to an increase in the stability of their microtubules, a condition necessary for the formation of long neurites (FIG. 5).

Effect of Steroids on the Cytotoxicity of Okadaic Acid

Figure 6:
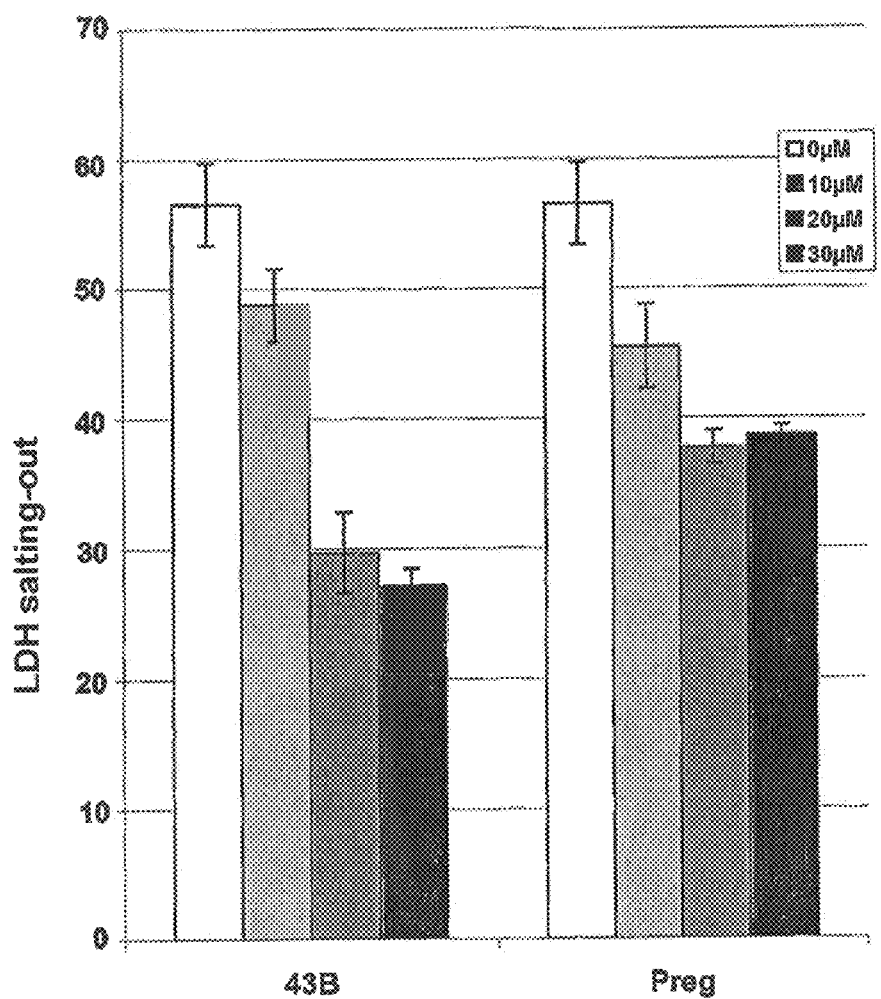
FIG. 6: Toxicity of okadaic acid. Steroid protection. Human neuroblastoma HS-SY5Y cells were cultured for 24 hours in the presence of okadaic acid only or associated with increasing concentrations of PREG or 3-methoxy-PREG. Cell death was indicated by the release of lactate dehydrogenase (LDH) in the culture medium.

Okadaic acid is a protein phosphatase inhibitor. Thus, the hyperphosphorylation of tau protein is implicated in microtubule depolymerization and in human neuroblastoma HS-SY5Y cell death. The exposure of SY5Y cell cultures to okadaic acid does in fact cause significant cell death. Cell death is decreased by the simultaneous addition of PREG and the same effect, only much stronger, is seen by the simultaneous addition of 3-methoxy-PREG (43B) (FIG. 6).

Example 4

Tests of Toxicity

Cellular Toxicity

Cellular toxicity tests are carried out routinely on the PC12 cell line. The initial results show that PREG and 43B do not demonstrate toxicity at concentrations as high as their solubility limits (approximately 50 μM).

In Vivo Toxicity

In rats, the daily injection for one month of 48 mg/kg of 43B (which is 4 time the active dose for spinal cord trauma) affected neither average weight nor behavior.

Example 5

In Vivo Experiments—Spinal Cord Trauma

Spinal Cord Contusion Model

To determine the neuroprotective effects of the molecules tested, a spinal cord compression model is used. This model involves the total paralysis of the animals in the first few days following the operation. This period of paralysis is followed of a phase of approximately three weeks during which the animals partially recover their motor function. The study of this recovery using a simple and precise functional test based on observation of the animals (the BBB score) makes it possible to study the speed and the degree of recovery of the animals, with and without treatment.

Figure 7:
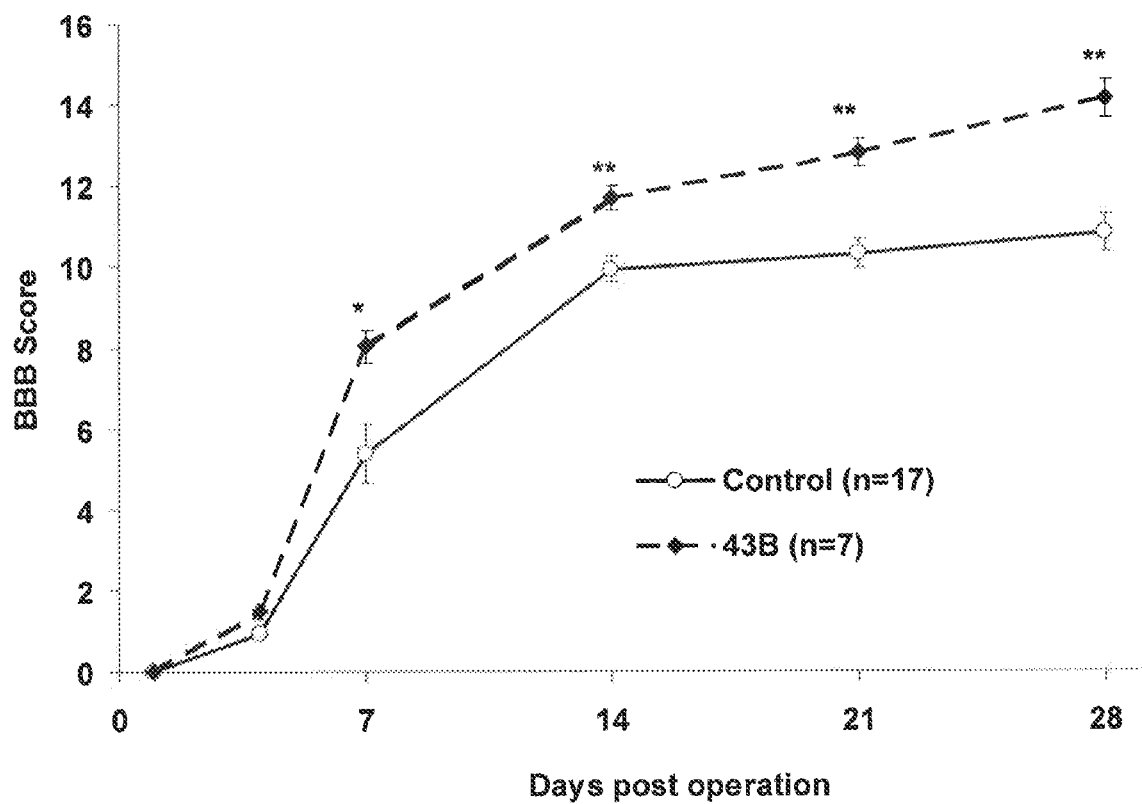
FIG. 7: Effect of molecule 43B on locomotor recovery following spinal cord compression in rats. Animal locomotion was evaluated in a blind format during the 1-28 day post-operative period using the BBB score which evaluates the degree of paralysis (higher values correspond to better recovery). Statistical significance: * indicates $p<0.001$; ** indicates $p<0.0001$.

Two groups of rats were subjected to spinal cord compression. Then, daily for 2 weeks, the animals received a subcutaneous injection containing either sesame oil alone (control group, n=20), or sesame oil containing molecule 43B (43B group, n=20; 12 mg/kg/day). The first injection was given 5 minutes after spinal cord compression. Locomotion of the animals, using BBB scores, was evaluated in a blind format on post-operation days 1, 4, 7, 14, 21, and 28. Three animals in each group had to be excluded from the study. Statistical analysis of the results using the nonparametric Mann-Whitney test shows that the animals treated with 43B present results quite significantly higher than the control animals as of post-operation day 7 (FIG. 7).

Example 6

In Vivo Experiments—Cerebral Ischemia

Two models of cerebral ischemia in the rat were developed.

The first is a permanent or transient focal ischemia model of the middle cerebral artery using electrocoagulation or clamping (evaluation of neuroprotection by quantification of the volume of the lesioned area).

The second is a transient global cerebral ischemia model. This model is created in the rat by electrocoagulating and severing the vertebral arteries and then clamping the carotid arteries for a period of 15 minutes (evaluation of neuroprotection and cerebral plasticity increase by quantification of neuronal loss in the CA1 region of the hippocampus and by memory tests).

Example 7

In Vivo Experiments—Alzheimer-Type Neurodegenerative Disease Model (Transgenic Mice)

In order to evaluate the therapeutic potential of 433 to treat Alzheimer-type neurodegenerative diseases, a homozygous transgenic line of mice, such as described by Götz (EMBO J. 1995; 14(7):1304-13), can be used.

These mice express the longest human tau protein isoform. They present symptoms of neurological dysfunction expressed as muscular weakness and a reduction in motor coordination which correlate histologically with the appearance of abnormal neurites and hyperphosphorylated tau proteins as is seen in Alzheimer's disease. This pathological phosphorylation decreases the affinity of tau for microtubules and favors its aggregation.

By treating these mice with molecules that increase microtubule stability, it is intended that the proportion of tau protein associated with the microtubules is increased and thus the appearance of symptoms is delayed.

Figure 8:
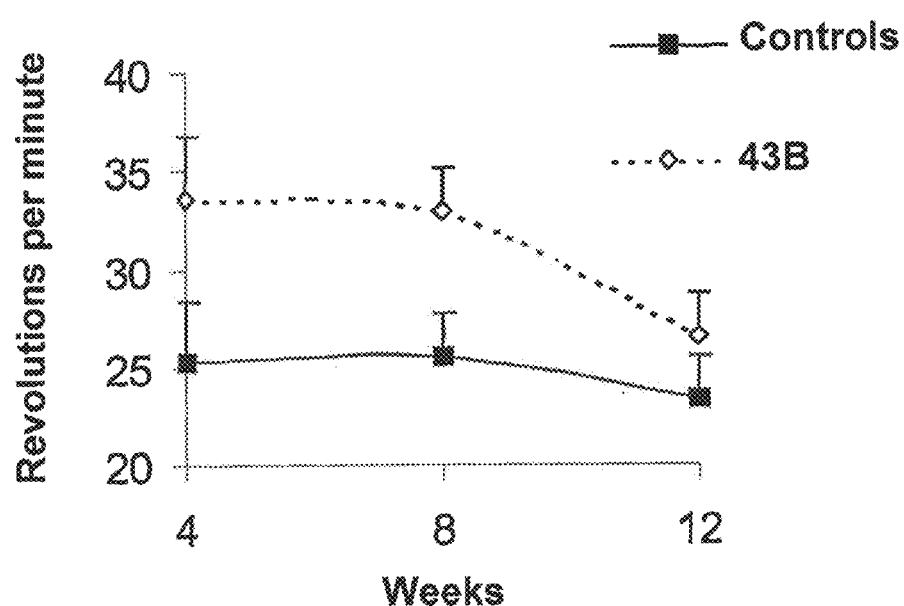
FIG. 8: Effect of molecule 43B on the motor incoordination of transgenic mice expressing the longest isoform of human tau protein in their neurons. Motor incoordination was evaluated in a blind format during 12 weeks following subcutaneous insertion of an implant that was empty or contained either PREG or 3-methoxy-PREG (43B). The maximum speed of rotation of the RotaRod drum before the rat falls is a measurement of motor coordination (higher values correspond to a better treatment effect).

A breeding program was undertaken at Bicêtre and genotyping made it possible to select mice homozygous for the transgene. At the age of 21±3 days, 3 groups of 10 mice were assembled and each group then received subcutaneously either an empty implant, an implant of PREG, or an implant of 3-methoxy-PREG. The implants released 0.38 mg of steroid per day for 90 days. The progression of motor incoordination was followed by repeated RotaRod tests. Only the 3-methoxy-PREG had a beneficial effect on motor dysfunction (FIG. 8).

Example 8

In Vivo Experiments—Mnemonic Performance

Mnemonic Deficit Induced by Colchicine

Colchicine, a substance which depolymerizes microtubules without blocking protein synthesis, is injected at very low doses that do not induce neuronal death in the rat hippocampus. These injections cause a learning deficit which results from lasting microtubule depolymerization. The objective is to test the effect of microtubule-stabilizing molecules on mnemonic deficits and histological lesions in the hippocampus induced by colchicine.

Mnemonic Deficit During Ageing

Studies on ageing are carried out on old rata presenting mnemonic deficits. The objective of this experiment is to mitigate these deficits by a chronic treatment with our molecules.

The two-step memory experiments are based on the spontaneous exploration of novelty and are adapted from the experiments described by Dellu et. al. (1992, Brain Res., 588, 132-9) and Ladurelle et al. (2090, Brain Res., 858, 371-9). The technical instructions from these two publications concerning spatial memory tests using labyrinths are included in reference to the present application.

Example 9

Pharmacokinetics

The pharmacokinetics of the molecules tested in vivo are evaluated using gas chromatography/mass spectrometry (GC/MS) assays.

A study was conducted with PREG and molecule 43B. Its primary objective was to show that molecule 43B crossed the blood-brain barrier.

Rats were injected with either PREG or 43B diluted in sesame oil and assayed by GC/MS for the quantity of PREG or 43B in various organs at 1, 4, 8, and 24 hours after injection (12 mg/kg, in 0-5 ml of sesame oil; subcutaneous injection).

Figure 9:
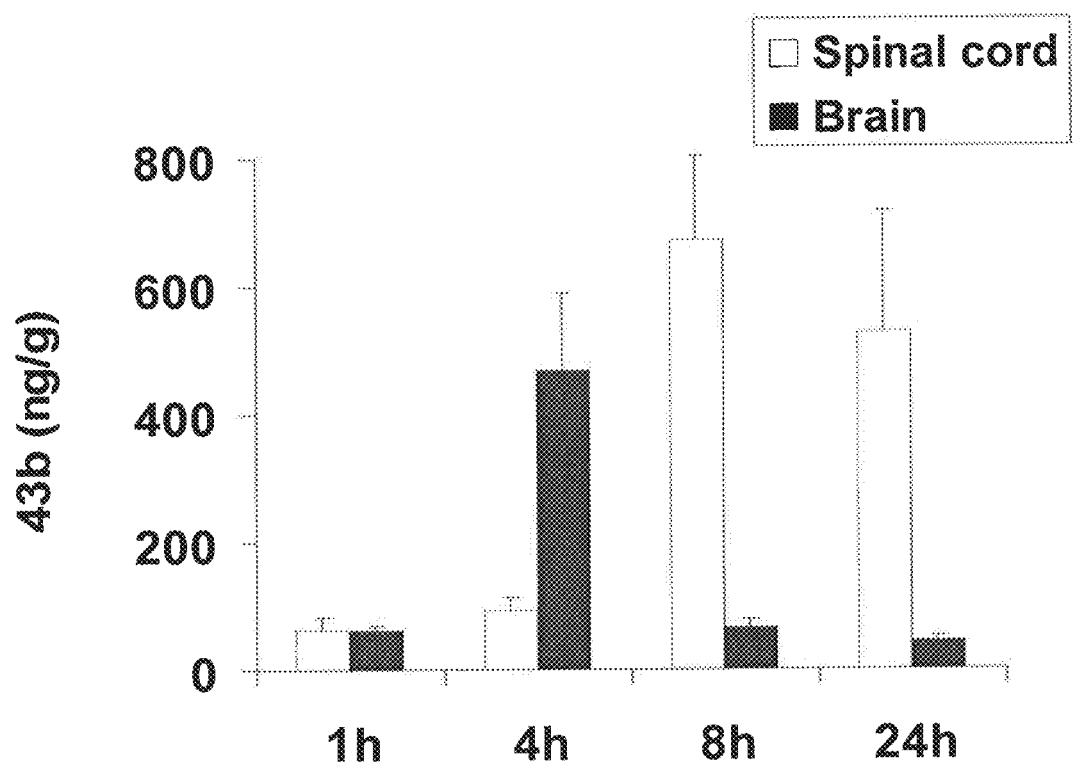
FIG. 9: Kinetics of the appearance of 3-methoxy-PREG (43B) in rat brain and spinal cord following subcutaneous injection of 43B (12 mg/kg) in a sesame oil solution.

The results presented in FIG. 9 show that molecule 43B penetrates rapidly into the spinal cord and the brain of the injected rats, and tends to accumulate there.

These results obtained in vitro and in vivo clearly demonstrate that molecule 43B (3-methoxy-PREG) gives spectacular results on the growth of neurites in culture and on the spinal cord compression model.

Example 10

Other Molecules According to the Invention

The indices of binding and activity are expressed as a percent of PREG.

Binding (affinity) is measured by the displacement of PREG-$^3$H.

Activity is measured by the increase in optical density at 345 nm of a mixture of purified tubulin and MAP2, incubated at 37° C. in the presence of GTP.

Stimulation of neuritic sprouting is conducted on PC12 cells differentiated in the presence of NGF (10 ng/ml) and the steroid being tested (30 μM) for 3 days. For each condition, the average length of the longest 200 neurites in each cell is measured simultaneously for 3 cultures.

The results are represented in Table 1 below by one, two or three crosses (+) according to whether stimulation is lower than, equal to or higher than that produced by PREG.

TABLE 1

Indices of binding and activity of other molecules, expressed as a percent of PREG

| Steroid | Affinity | Activity | Neuritic sprouting |
|---|---|---|---|
| Pregnenolone (PREG) | 100 | 100 | ++ |
| 3β-methoxy-pregna-5-ene-20-one (3-methoxy-PREG) | 100 | 100 | +++ |
| 3β-methoxy-pregna-5-ene-20-one-17α-dichloromethyl | 53 | 113 | +++ |
| 3β-methoxy-5α-pregnane-20-one | 87 | 10 | +++ |
| 3β-methoxy-5α-pregnane-20β-ol | 65 | 65 | ++ |
| PREG-16α-methyl | 80 | 70 | ++ |
| PREG-16β-methyl | 63 | 67 | (++) |
| 3β-methoxy-pregna-5,14-diene-20-one | 102 | 50 | + |
| PREG-16α,17α-epoxy | 41 | 54 | + |
| PREG-16α,17α-methylene | 62 | 49 | + |
| Pregna-5-ene-3β,20β-diol-20-acetate | 60 | 108 | ++ |
| 3β-hydroxy-5α-pregnane-20-one-16α-methyl | 57 | 53 | (+) |

These results show the effectiveness op other molecules derived from pregnenolone to stimulate the polymerization of microtubules induced by MAP2 end to stimulate neuritic sprouting. For those that are not 3β-methyl derivatives, it is foreseeable that these derivatives will at least maintain their activity.

Example 11

Activity of 3-Methoxy-Pregnenolone on Progesterone Receptor

The capacity of 3-methoxy-pregnenolone to display progesterone activity, and thus to be considered as a progestin, was tested by assaying the activity of 3-methoxy-pregnenolone on progesterone receptor.

Indeed, progesterone is an agonist of progesterone receptor, as are all progestins. In contrast, compounds able to inhibit progesterone activity on its receptor are called progesterone receptor antagonists.

Methods

The main experimental setting used is the following: HEK293T cells were transiently transfected, using calcium phosphate precipitation technology, with expression receptors pSG5hPR (which permits expression of human progesterone receptor (PR)), pFC31-luc (contains the luciferase gene under the control of the MTV promoter, which is in turn activated by binding of a progestin to progesterone receptor) and pcbetagal (which permits expression of betagalactosidase), and cultured during 24 hours with increasing amounts of various compositions:

1. Test of progesterone receptor agonist activity: transfected cells were cultured with increasing amounts of progesterone or 3-methoxy-pregnenolone With this setting, a compound with progesterone receptor agonist activity permits a transactivation activity resulting in the expression of luciferase (since the binding of a progestin to PR results in activation of the MMTV promoter, which directs the expression of luciferase).

In contrast, a compound without progesterone receptor agonist activity does not permit a transactivation activity and luciferase is not expressed (since PR is not activated and thus does not activate the MTV promoter);

2. Test of progesterone receptor agonist activity: transfected cells were cultured with progesterone (1 nM) and increasing amounts of RU486 (a well-known progesterone receptor antagonist) or 3-methoxy-pregnenolone.

With this setting, a compound with progesterone receptor antagonist activity competes with progesterone for the occupation of progesterone receptor and results in a progressive loss of transactivation activity when the amount of this compound is increased compared to progesterone.

Results

Figure 10:
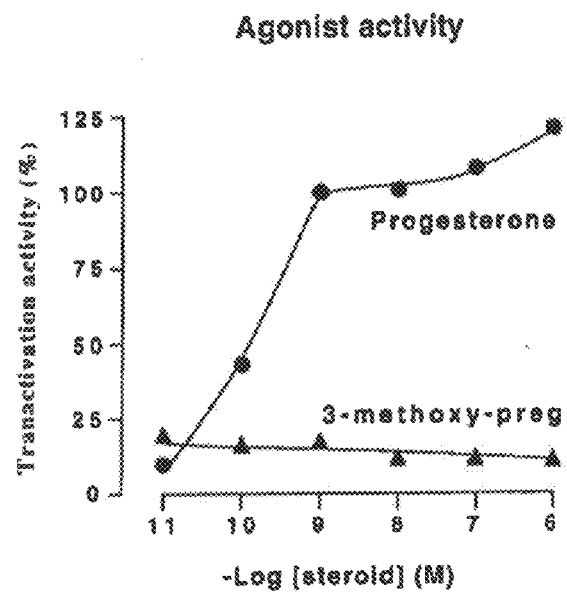
FIG. 10: Test of progesterone receptor agonist activity.

The results obtained with experimental setting 1 (test of progesterone receptor agonist activity) are displayed in FIG. 10.

FIG. 10 clearly shows that, contrary to progesterone, which permits a transactivation activity leading to the expression of luciferase, 3-methoxy-pregnenolone does not permit such a transactivation activity, even at the highest tested concentrations, thus demonstrating that 3-methoxy-pregnenolone does not have progesterone receptor agonist activity, and cannot thus be considered as a progestin.

Figure 11:
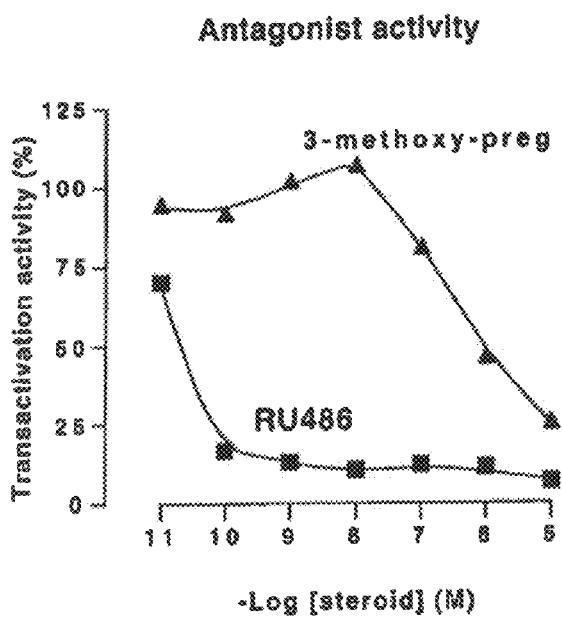
FIG. 11: Test of progesterone receptor antagonist activity.

The results obtained with experimental setting 2 (test of progesterone receptor antagonist activity) are displayed in FIG. 11.

These results unambiguously show that even if 3-methoxy-pregnenolone does not have the very high antagonist activity of RU486, it is a weak progesterone receptor antagonist.

Example 12

In Vivo Experiments—Treatment of Depression

Microtubule Dynamics

Acute Effects of Pregnenolone (PREG) and 3-Methoxy-PREG (43B) Administration on Microtubule Dynamics in Rat Hippocampus.

Adult male (250-300 g) Sprague Dawley rats received a single injection of pregnenolone (PREG) and 3-methoxy-PREG (43B). The effects produced by neurosteroids were compared with those produced by acute administration of the antidepressant drug fluoxetine (selective serotonin reuptake inhibitor SSRI).

Figure 12:
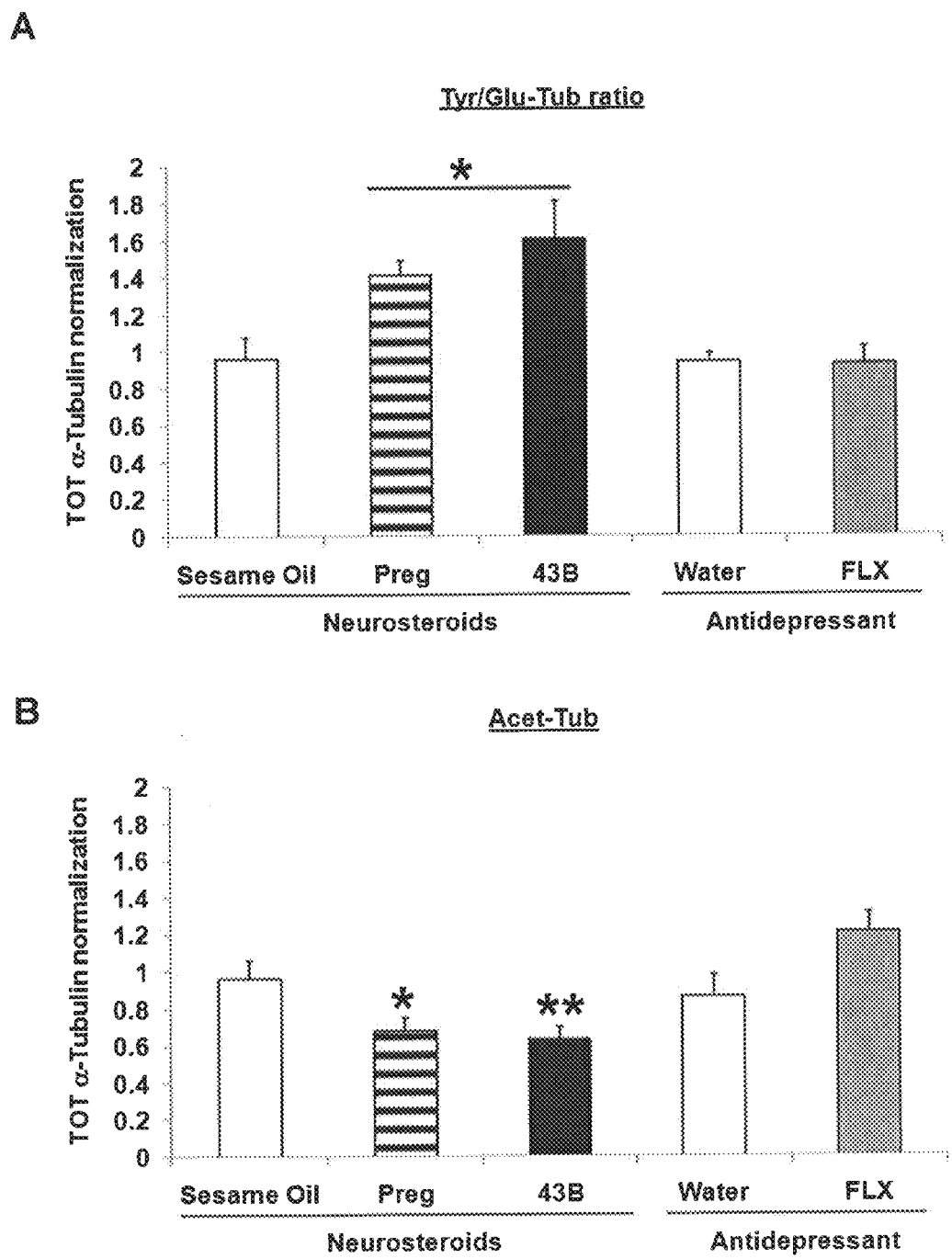
FIG. 12: A single administration of pregnenolone (PREG) and 3-methoxy-PREG (43B) (10 mg/kg subcutaneously) increased microtubule dynamics in rat hippocampus, but a single administration of the antidepressant fluoxetine (FLX) (10 mg/kg subcutaneously) did not (A) PREG and 43B induced a significant increase in Tyr/Glu-Tub ratio (index of microtubule dynamics), but FLX did not, (B) PREG and 43B induced a significant decrease in Acet-Tub (marker of stable microtubules), while FLX showed a tendency to increase it. Mean±SEM, n=6 per group. **$P<0.01$, *$P<0.5$ vs sesame oil.

A single administration of PREG (10 mg/kg subcutaneously) or 3-methoxy-PREG (10 mg/kg subcutaneously) significantly increased the ratio between the dynamic tyrosinated α-tubulin and the stable detyrosinated α-tubulin (Tyr/Glu-Tub ratio) in rat hippocampus 3 h following injection (FIG. 12A). Additionally, the stable acetylated α-tubulin (Acet-Tub) was significantly decreased by both PREG and 43B (FIG. 12B). These findings suggest increased microtubule dynamics and function and indicate a potential acute promoting effect of 43B on hippocampal structural neuronal plasticity. In contrast, acute fluoxetine did not change Tyr/Glu-Tub ratio (FIG. 12A) and showed a tendency to increase Acet-Tub (FIG. 12B). These data are in line with previous reports showing a promoting effect of such antidepressant drug only following chronic administration (Warner-Schmidt and Duman, *Hippocampus* 2006). Therefore, 43B showed the interesting potential to be more effective and quicker than antidepressant drugs in correcting neuronal structural alterations associated with major depression.

Neurosteroids and 3-Methoxy-PREG (43B) Levels

Pregnenolone (PREG) and progesterone (PROG) levels in rat plasma and hippocampus 3 h following acute administration of sesame oil (250 μl/rat subcutaneously, n=6) or 43B (10 mg/kg subcutaneously, n=6) are shown in Table 2 below.

TABLE 2

PREG and PROG levels in rat plasma and hippocampus 3 h following acute administration of sesame oil or 43B

| Treatment | Plasma (ng/ml) | | Hippocampus (ng/g) | |
| --- | --- | --- | --- | --- |
| | PREG | PROG | PREG | PROG |
| Sesame oil | 1.15 ± 0.22 | 0.86 ± 0.23 | 40.13 ± 13.33 | 1.37 ± 0.20 |
| 43B | 1.33 ± 0.34 | 0.66 ± 0.20 | 36.22 ± 7.24 | 1.47 ± 0.16 |

As expected 43B was not converted back to PREG or metabolized to PROG

Additionally, in the same 43B injected animals, the concentrations of the drug were 21.11±5.04 ng/ml in plasma and 73.3±14.68 ng/g in hippocampus 3 h following injection.

Forced Swimming Test (FST): Assessing the Antidepressant Activity of 3-methoxy PREG (43B)

The present experiment investigated the antidepressant effects of pregnenolone (PREG) and 3-methoxy-PREG (43B) compared to those exerted by fluoxetine and desipramine. Adult male (250-300 g) Sprague Dawley rats were randomly assigned to different experimental groups as follow: i) Controls: Water (250 µl/rat subcutaneously, n=6); Sesame Oil (250 µl/rat subcutaneously, n=12); ii) Antidepressants: Fluoxetine (FLX) (10 mg/kg subcutaneously, n=6), Desipramine (DMI) (10 mg/kg subcutaneously, n=6); iii) Neurosteroids: Pregnenolone (PREG) (10 mg/kg subcutaneously, n=12), 3-methoxy-Preg (43B) (10 mg/kg subcutaneously, n=12). Drugs were administered following the traditional dosing regimen used in the FST consisting of three injections: 24, 5, 1 h before testing.

The FET is currently the most widely used animal model for assessing depression related behavior and antidepressant drug activity in rodents (Cryan et al., *Neubiorev.* 2005). Rats are placed in an inescapable cylinder of water where they develop an immobile posture believed to reflect a "depressive"-like state. The Lime rats spend immobile is decreased by drugs exerting antidepressant activity.

Additional behaviors can be detected in the FST; namely, climbing and swimming. It has been shown that swimming behavior is sensitive to SSRIs such as fluoxetine whereas climbing is sensitive to norepinephrine re-uptake inhibitors (NRI) such as desipramine.

Figure 13:
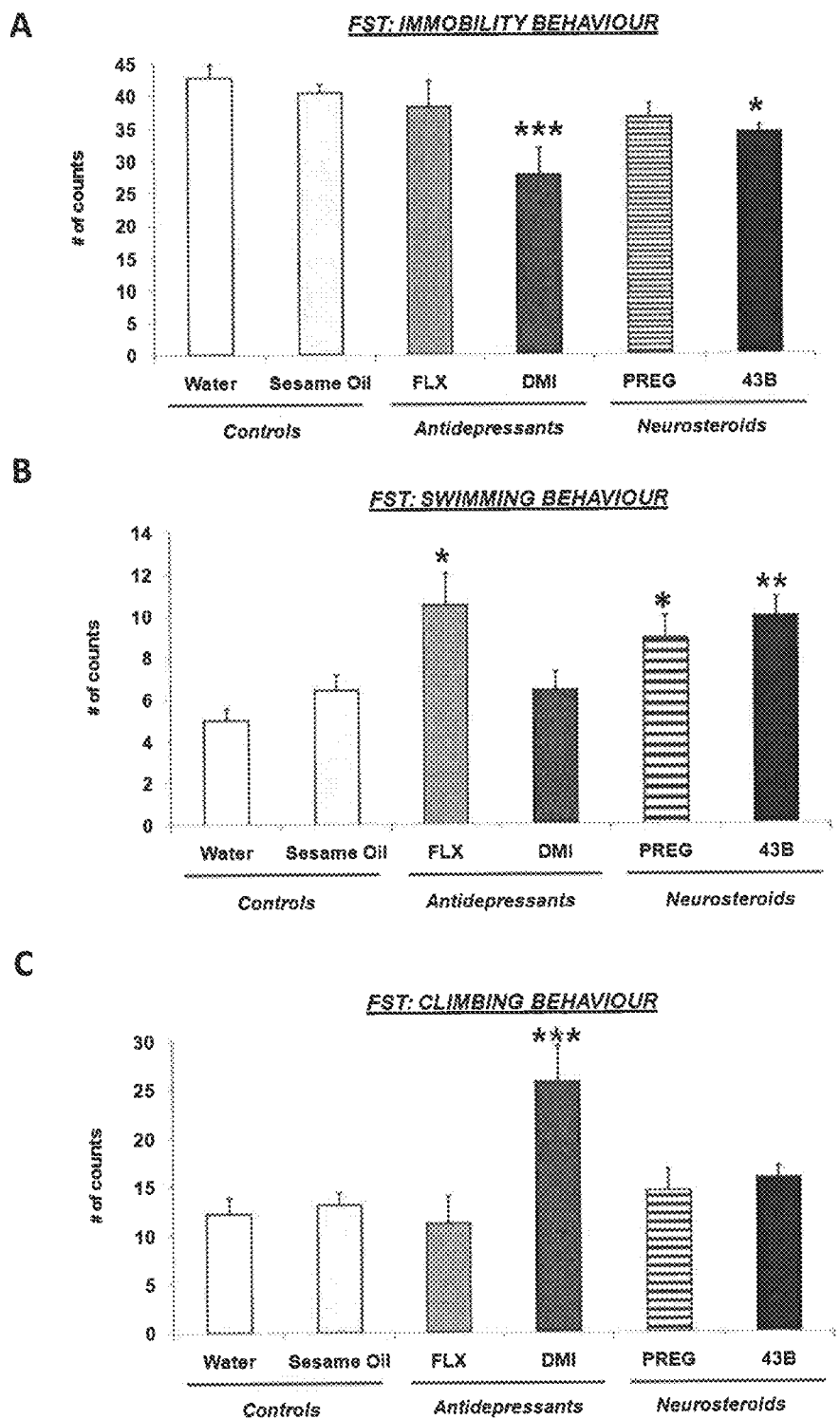
FIG. 13: Antidepressant effects of pregnenolone (PREG) and 3-methoxy-PREG (43B) compared to those of the antidepressant drugs fluoxetine (FLX) and desipramine (DMI) in rats. (A) 3-methoxy-PREG (43B) decreased rat immobility in the FST showing antidepressant activity. Results are expressed as mean±SEM (n=6-14). One-way ANOVA: Treatment (F5, 46: 4.30 $P<0.01$), ***$P<0.001$, *$P<0.05$ vs, water and sesame oil (Fisher LSD test), (B) FRED and 3-methoxy-PREG (43B) increased rat swimming in the EST showing a fluoxetine-like (serotonin re-uptake inhibitor) profile. Results are expressed as mean±SEM (n=6-14). One-way ANOVA: Treatment (F5, 46: 3.57 $P<0.01$). **$P<0.01$, *$P<0.05$ vs. water and sesame oil (Fisher LSD test). (C) 3-methoxy-PREG (43B) did not affect rat climbing in the FST showing. One-way ANOVA: Treatment (F5, 46: 3.57 $P<0.01$). **$P<0.01$, *$P<0.05$ vs. water and sesame oil (Fisher LSD test).

Results showed that 43B significantly decreased rat immobility in the FST, suggesting a potential antidepressant activity of the drug (FIG. 13A).

In addition, both PREG and 43B significantly increased rat swimming in the FST showing a fluoxetine-like profile (FIG. 13B), since rat climbing behavior was not changed (FIG. 13C).

Novel Object Recognition Test (NOR): Assessing Cognitive Effects of 3-Methoxy-PREG (43B)

Cognitive dysfunction, including impaired recognition memory, are common features in depressed patients (Egeland et al., *Scand. J. Psychol.* 2005). The present experiment explored the ability of 3-methoxy-PREG (43B) administration to increase recognition memory retention in naive animals and to recover recognition memory deficits in animals submitted to the social isolation protocol. Rearing rats in isolation from the time of weaning and throughout adulthood can induce a series of hippocampal structural and molecular deficits paralled by behavioural alterations resembling a depressive-like state (Weiss and Feldon, *Psychopharmacology* 2001; Bianchi et al., *EJN* 2006). Recognition memory was assessed using the NOR test which is a two-trial test of recognition memory based on the spontaneous preference of rats for novelty (Ennaceur and Delacour, *Behav. Brain. Res.* 1988; Bianchi et al. *EJN.* 2006). Briefly, rats are placed in the open field arena for a 3 min period of habituation and then re-placed in their "home" cage for 1 min. The animals are then re-placed in the arena for the familiarization trial (T1) and allowed to explore two identical objects for 5 min. Following a variable Inter-trial interval (ITI), rats are then submitted to the choice trial (T2) and exposed to one of the two objects explored during T1 (familiar object) and to a novel object. The ability of the animals to discriminate between the novel and the familiar object is then expressed as D2-INDEX: [novel object (sec)–familiar object (sec)]/[novel object (sec)+familiar object (sec)] (Ennaceur and Delacour, *Behav. Brain. Res.* 1988). Adult male Sprague Dawley rats (350-400 g) discriminated between the familiar and the novel object following 1 min and 1 h ITI (D2-INDEX of 0.48±0.06 and 0.56±0.04, respectively), in contrast, following 4 h of ITI rats showed delay-induced deficits in recognition memory (D2-INDEX of 023±006).

Test 1

3-Methoxy-PREG (43B) Increased Memory Retention in Naïve Animals

A constant ITI of 4 h. was used. Adult male Sprague Dawley rats (350-400 g) were randomly divided in two experimental groups and received: i) sesame oil (250 µl subcutaneously; n=12) or ii) 43B (10 mg/kg subcutaneously; n=11) immediately after the familiarization trial (T1).

Figure 14:
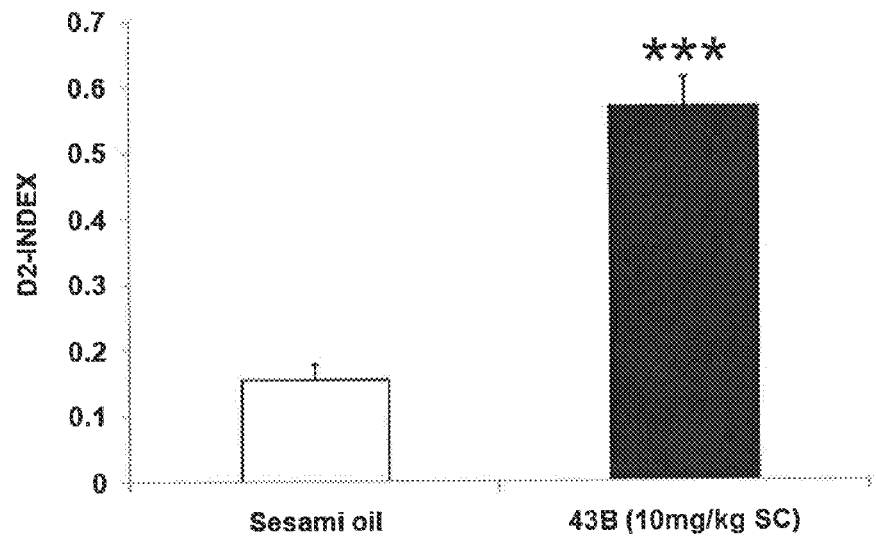
FIG. 14: 3-methoxy-PREG (43B) enhanced retention of recognition memory in naïve an and recovered recognition memory deficits in social isolated rats. (A) Sesame Oil treated rats cannot discriminate between the novel and the familiar object following a 4 h inter trial interval (ITI) time. In contrast, 43B (10 mg/kg subcutaneously) treated rats retain the ability to discriminate between the novel and the familiar object. Mean±SEM, n=11-12 per group. ***$p<0.001$ vs sesame oil (T-test). (B) Isolated animals treated with sesame oil cannot discriminate between the novel and the familiar object following 1 ITI, while grouped (control) rata clearly discriminate, 1 contrast, isolated animals receiving a single injection of 43B (10 mg/kg subcutaneously) its before performing the task, recovered such recognition memory deficits.
Figure 14:
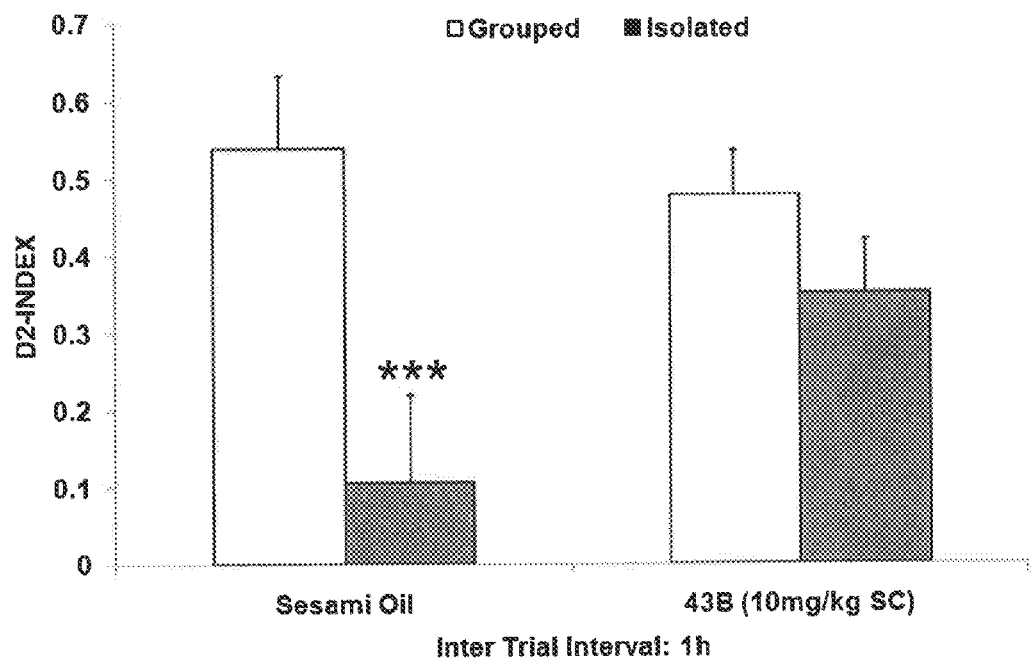

Sesame oil treated rats did not discriminate between the novel and the familiar object following a 4 h ITI. In contrast, 43B (10 mg/kg subcutaneously) treated rats discriminated between the novel and the familiar object showing increased memory retention. (FIG. 14A).

The present data clearly show the ability of 3-methoxy-PREG (43B) administration (10 mg/kg subcutaneously) to enhance retention of recognition memory in the NOR test confirming the potential use of 3-methoxy-PREG in the therapy of cognitive symptoms associated with psychiatric and/or neurodegenerative disorders.

Test 2

3-Methoxy-PREG (43B) Induced Recovery of Memory Deficit in Social Isolated Animals Male Sprague Dawley rats (post-natal day 25-28) were singly housed (isolated animals, n=14) or housed in groups of 4 per cage (grouped animals, n=14) for 8 weeks. The NOR test was performed using a constant ITI of 1 h: a) Isolated (n=7) and grouped (n=7) rats received one injection of sesame oil (250 µl subcutaneously); b) isolated (n=7) and grouped (n=7) rats received one injection of 3-methoxy-PREG (43B) (10 mg/kg subcutaneously) injections were made 1 h before animals performed the NOR task.

Control grouped animals (sesame oil injected), as expected, discriminated between the novel and the familiar object following a 1 h ITI, but isolated rats did not (FIG. 14B). However, isolated rats injected with 43B (10 mg/kg subcutaneously) efficiently discriminated between the familiar and the novel object (FIG. 14B).

Conclusions

A single injection of 3-methoxy-PREG (43B) resulted in an hippocampal concentration of the drag of 73.3±14.68 ng/g of tissue and significantly increased the expression of markers of microtubule dynamics in rat hippocampus. These effects may lead to hippocampal structural neuronal remodeling and formation of new synaptic connections suggesting the potential use of 43B in the therapy of neuropsychiatric disorders characterized by hippocampal structural neuronal alteration and synaptic deficits such as depression. Accordingly, the molecule was tested in an animal model widely used to test the antidepressant properties of novel drugs such as the forced swimming test and showed a clear antidepressant efficacy similar to that of the antidepressant fluoxetine (SSRI). Furthermore, a single injection of 43B can enhance retention of recognition memory in naïve animals and recover recognition memory deficits in animals submitted to social isolation which is a putative animal model of depression. Taken all together, our data strongly indicate that 43B possess antidepressant efficacy accompanied by cognitive enhancing properties. These peculiar characteristics suggest 43B as a promising new pharmacological tool for the treatment of major depression and major depression subtypes such atypical depression, melancholic depression, psychotic depression and geriatric depression. Other subtypes include dysthymia, postpartum depression, post stroke depression, and subcortical ischemic depression.

Example 13

3-Methoxy-PREG has No Androgenic, Estrogenic, Glucocorticoid and Mineral Corticoid Activity Binding affinity of 3-methoxy-PREG (MAP4343) for receptors of steroid hormones was evaluated using radioligand binding essays.

MAP4343 (10 μM) was ineffective (<25% inhibition) in displacing specific radioligands from the following binding sites; Mineralocorticoid Receptor (MR), Androgen Receptor (AR), Estrogen. Receptors (ERα and ERβ) and Glucortiocid Receptor (GR). The results are summarized below in Table 3 below.

TABLE 3

Affinity of MAP4343 (10 μM) for steroid hormones receptors measured by radioligand binding assays. Biochemical assay results are presented as the percent inhibition of specific binding (significant responses: ≥50% inhibition). None of the results met significance criteria at concentrations used.

| Target | Ligand | Source | % inhibition* |
|---|---|---|---|
| MR | 4.5 nM [$^3$H] D-Aldosterone | Wistar Rat kidney | 25 |
| AR | 1.5 nM [$^3$H] Mibolerone | Rat recombinant E. coli | 18 |
| ERα | 0.5 nM [$^3$H] Estradiol | Human recombinant Sf9 cells | −8 |
| ERβ | 0.5 nM [$^3$H] Estradiol | Human recombinant Sf9 cells | 16 |
| GR | 3 nM [$^3$H] Dexamethasone | Human HeLa S3 cells | 21 |

*Negative values correspond to stimulation of binding or enzyme activity

Example 14

3-Methoxy-PREG has No Significant Affinity for Receptors of the Central Nervous System MAP4343 has been screened for in vitro affinity to 80 different CNS neurotransmitters receptors using various validated binding assays.

The results show that MAP4343 has no significant affinity for any tested receptor including the ones traditionally associated with side effects or abuse liability. Results are summarized in following Table 4.

TABLE 4

In vitro affinity of MAP4343 (10 μM) for CNS neurotransmitter receptors associated with side effects and/or abuse liability. Data are the average of two individual assays for each receptor and are expressed as % inhibition of the control specific binding of the reference compound. Results showing an inhibition higher than 50% are considered to represent significant effects of the test compound. MAP4343 showed no significant effects on any of the tested receptor at the concentration used.

| Receptor family | Target | Ligand | Source | % Inhibition of control specific binding |
|---|---|---|---|---|
| Muscarinic (Cholinergic) | $M_1$ | [$^3$H] pirenzepine | Human recombinant (CHO cells) | −3 |
| | $M_2$ | [$^3$H] AF-DX 384 | Human recombinant (CHO cells) | 20 |
| | $M_3$ | [$^3$H] 4-DAMP | Human recombinant (CHO cells) | 3 |
| | $M_4$ | [$^3$H] 4-DAMP | Human recombinant (CHO cells) | 20 |
| | $M_5$ | [$^3$H] 4-DAMP | Human recombinant (CHO cells) | 12 |
| Histaminergic | $H_1$ | [$^3$H] pyrilamine | Human recombinant (HEK-293 cells) | 9 |
| | $H_2$ | [$^{125}$I] APT | Human recombinant (CHO cells) | −21 |
| Noradrenergic | $\alpha_1$ | [$^3$H] prazosin | rat cerebral cortex | 4 |
| | $\alpha_2$ | [$^3$H] RX 821002 | rat cerebral cortex | 7 |
| | $\beta_1$ | [$^3$H] (−) CGP 12177 | Human recombinant (HEK-293 cells) | 1 |
| | $\beta_2$ | [$^3$H] (−) CGP 12178 | Human recombinant (CHO cells) | −4 |
| | Transporter | [$^3$H] nisoxetine | Human recombinant (CHO cells) | 3 |
| Serotoninergic | 5-$HT_{1A}$ | [$^3$H] 8-OH-DPAT | Human recombinant (HEK-293 cells) | 2 |
| | 5-$HT_{1B}$ | [$^{225}$I] CYP + (−) propranolol | rat cerebral cortex | 4 |
| | 5-$HT_{2A}$ | [$^3$H] ketanserin | Human recombinant (HEK-293 cells) | 1 |
| | 5-$HT_{2B}$ | [$^{125}$I] (±) DOI | Human recombinant (CHO cells) | −4 |
| | 5-$HT_{2C}$ | [$^3$H] mesulergine | Human recombinant (CHO cells) | 7 |
| | 5-$HT_3$ | [$^3$H] BRL 43694 | Human recombinant (CHO cells) | 10 |
| | 5-$HT_{5A}$ | [$^3$H] LSD | Human recombinant (CHO cells) | −5 |

TABLE 4-continued

In vitro affinity of MAP4343 (10 μM) for CNS neurotransmitter receptors associated with side effects and/or abuse liability. Data are the average of two individual assays for each receptor and are expressed as % inhibition of the control specific binding of the reference compound. Results showing an inhibition higher than 50% are considered to represent significant effects of the test compound. MAP4343 showed no significant effects on any of the tested receptor at the concentration used.

| Receptor family | Target | Ligand | Source | % Inhibition of control specific binding |
|---|---|---|---|---|
| | $5\text{-HT}_6$ | [$^3$H] LSD | Human recombinant (CHO cells) | 12 |
| | $5\text{-HT}_7$ | [$^3$H] LSD | Human recombinant (CHO cells) | −11 |
| | Transporter | [$^3$H] imipramine | Human recombinant (CHO cells) | 3 |
| Dopaminergic | $D_1$ | [$^3$H] SCH 23390 | Human recombinant (CHO cells) | 2 |
| | $D_{2S}$ | [$^3$H] spiperone | Human recombinant (HEK-293 cells) | 6 |
| | $D_3$ | [$^3$H] spiperone | Human recombinant (CHO cells) | 8 |
| | $D_{4.4}$ | [$^3$H] spiperone | Human recombinant (CHO cells) | 6 |
| | $D_5$ | [$^3$H] SCH 23390 | Human recombinant (GH4 cells) | −7 |
| | Transporter | [$^3$H] BTCP | Human recombinant (CHO cells) | |
| GABA | (non-selective) | [$^3$H] GABA | rat cerebral cortex | 2 |
| NMDA | PCP site | [$^3$H] TCP | rat cerebral cortex | −10 |
| Cannabinoid | $CB_1$ | [$^3$H] CP 55940 | Human recombinant (CHO cells) | 12 |
| Oppioid | $\delta_2$ | [$^3$H] DADLE | Human recombinant (CHO cells) | −3 |
| | x | [$^3$H] 0 69593 | rat recombinant (CHO cells) | 19 |
| | μ | [$^3$H] DAMGO | Human recombinant (HEK-293 cells) | 0 |

Example 15

Efficiency of 3-Methoxy-PREG Treatment on Traumatic Brain Injury (TBI) In Vivo

The efficiency of treatment with 3-methoxy-PREG (MAP4343) has been tested in vivo in rats in three different models of traumatic brain injuries.

Materials and Methods

1. TBI Models:

Male Sprague-Dawley rats of 170-200 body-weight are used. There were 12 animals, per group for all in vivo experiments (WET, MRI) except for the CHI injury which requested 17 animals per group because of the post-trauma mortality rate. Each group wee then split in two subgroups of 6 individuals for all post-mortem analysis (biochemical, histological and immunohistological analysis.

TBI models include the Controlled Cortical Impact (a focal severe lesion), the Closed Read Injury (a diffuse lesion) and the Lateral Fluid Percussion (a diffuse lesion).

1.1—Controlled Cortical Impact (CCI)

CCI was performed with an electromagnetic impact device as described (MyNeurolab, St. Louis, Mo.; Brody et al, 2007). Anesthesized rats were subjected to a single right lateral CCI, with the following parameters impact centered 4.0 mm anterior to lambda and 4.5 mm left of midline, within the craniotomy of the animal. The impact was set at a velocity of 4 m/s with a sustained depression of 200 ms, using a 5.0 mm tip.

1.2—Closed Head Injury (CHI)

The model "Closed Head Injury" (CHI), also commonly known as "weight-drop", "impact-acceleration" or Marmarou model, allows the induction of TBI on a closed skull and generates diffuse axonal injuries (Holtzer et al 2001). After anesthesia induction, the scalp was incised, a piece of metal (diameter 10 mm, height 3 mm)—designed to protect against skull fracture—was glued to the skull, between the lambda and bregma. The animal was then placed on a foam bed and a cylindrical metallic 230-g weight was dropped from 2 m through a metal tubing onto the disk. At the very moment of the impact, the head of the animal plunged briefly in the foam bed, which leads to an acceleration/deceleration of the brain inside the skull.

1.3—Lateral Fluid Percussion (LFP)

After anesthesia induction, the animal was placed on a stereotaxic frame. To expose the dura mater, craniotomy (diameter 5 mm) was under the left parietal cortex (−3.6 mm from Bregma, −3.0 mm from midline). A female Luer-Lock was placed over the craniotomy and was secured to the parietal bone with dental cement. The Luer-Lock was then filled with isotonic saline to create an interface with the dura meter.

Trauma was induced by a fluid percussion device (Custom Design and Manufacturing, United. Kingdom) (Besson et al., 2003) it is a cylindrical tank (60 cm long), with a piston on one side, over which a hammer exercises a constraint, and a male Luer-Lock on the other side. The female Luer-Lock was connected to the male Luer-Lock of the lateral fluid percussion device. The hammer was then released, resulting in a shift in the water column that produces a rapid increase in intracranial pressure of constant duration (20 msec), and a rapid and transient injection of isotonic saline into the epidural space. The amplitude of each shock wave was measured via a pressure transducer connected to the terminal portion of the device. The pressure signal was recorded on an oscilloscope. The variation of applied pressure was 1.6 to 2.4 atm, which corresponds to a moderate head injury.

The female Luer-Lock was then removed and the incision was sutured.

2. Water Exploration Test (WET): At Days 7 and 27 Post-Trauma

The WET test is a test avoiding immobility, in which rats have to swim if they do not want to drown: rats have to swim for 5 min in a quadrant from which they cannot exit, and what is measured is the velocity and the time pent in the central zone of this quadrant, considered as "anxiogenic". The less anxious is a rat, the more time it will, spend "floating" (null velocity) in the central zone (see Fares-2009).

More precisely, a circular tank (180 cm diameter, 60 cm high) is filled with water maintained at 27° C. to a depth of 40 cm. The water is made opaque by adding black gouache, allowing the VideoTrack system (ViewPoint) to detect the white-coloured rat. This tank is divided into 4 identical quadrants (6,358 cm2 each) using two 180 cm long opaque plastic separators. In each quadrant, one rat is introduced with its head facing the corner between the separator and the tank's wall. It is noteworthy to emphasize that 4 rats can be tested simultaneously using the 4 quadrants. Using the VideoTrack system, we draw two virtual areas: a large one delineates the whole quadrant in which the rat is placed; the so-called Full Quadrant (FQ) and a small one that delineates a central zone (CZ). The CZ, having the same shape as the FQ, measures 2,921 cm2, and is considered to be anxiogenic for animals. Thus, the distance, the number of entries, the time spent, and the velocity profile in the CZ are measured to assess anxiety-like behaviour. In addition, the total distance traveled in the FQ represents an indicator of motor activity. The duration of each trial is 5 minutes.

3. Magnetic Resonance Imaging (MRI): at Day 28 Post-Trauma

To determine lateral ventricle preservation, as well as lesion size (in the CCI model), T2-weighted MRI was performed 28 days after injury (D28). Acquisition was performed on a 7T Bruker AVANCE BIOSPEC—horizontal magnet, with rapid acquisition and relaxation enhancement (RARE).

Acquisitions were performed on anesthetized animals (isoflurane, with spontaneous ventilation). Body temperature was maintained at 3° C.

4. Brain Proteins: Studied at Day 35 Post-Trauma

Samples were analyzed by Western-blot at day 35 post-trauma (D35) to evaluate the effects of MAP4343 on: MAP2 (the target of MAP4343 and a modulator of microtubule function), the post-synaptic markers PSD95 and spinophilin, the pre-synaptic marker synaptophysin, and the axonal growth/integrity marker GAP43B.

Western blot was performed on cortex and hippocampus of TBI-injured animals receiving the first injection of MAP4343 (at 10 mg/kg or 20 mg/kg) or vehicle (sesame oil) 2 h after injury.

5. Histological Analysis of the Hippocampus Size: Studied at Day 35 Post-Trauma (D35)

Frozen sections were stained with cresyl violet. For each section analyzed, the size of the hippocampus was determined by first outlining all remaining tissue of each section taken at 500 μm intervals through the lesion (right hemisphere) or contra lateral hemisphere, thus providing a total tissue area (mm2) of the two hemispheres for each section. Then, the areas of sections were summed per hemisphere.

6. Administration of the Treatment and Measurement of MAP4343 in the Brain After Administration MAP4343 was dissolved in sesame oil and injected subcutaneously. Two distinct doses of MAP4343 (10 and 20 mg/kg) were tested in each model. The injection took place 2 h after trauma.

In order to establish whether TBI modifies the passage of MAP4343 into the brain, MAP4343 was measured by liquid chromatography associated to tandem mass spectrometry (LC-MS/MS) in the brain of animals sacrificed 6 h after CHI, LFP or CCI (4 h after MAP4343 single injection).

7. Immunohistological Analyses

Coronal sections were cut at 10 μm (seven sections by brain level).

After mounting on Superfrost slides, frozen sections were dried for 90 minutes at room temperature and stored at −80° C. until use. 10 μm sections were fixed with PFA solution for 30 min before incubation with anti-GFAP antibody, for the staining of astrocytes. The antibody was diluted at 1:1000. One series of sections from each brain was stained simultaneously, to reduce the variability in staining intensity. After immunohistochemistry, sections were digitized as grayscale images. Images were captured at a single sitting for each immunostained group of sections to further reduce the variability in the measurement of immunointensity. Immunostaining was quantitatively assessed by optical density measurements directly from the section image (Image J). Background was subtracted.

Results

The overview of the experimental set up used for studying the effect of 3-methoxy-PREG after traumatic brain injury (TBI) is displayed in FIG. 15.

Six key results have been obtained following treatment of rats submitted to various TBI models with 3-methoxy-PREG:
- 3-methoxy-PREG reaches the brain whatever the type of trauma,
- 3-methoxy-PREG decreases the anxiety induced by trauma,
- 3-methoxy-PREG reduces ventricular dilatation induced by trauma,
- 3-methoxy-PREG protects the hippocampus size integrity from the lesion induced by the trauma,
- 3-methoxy-PREG up-regulates neuronal brain markers of plasticity; and
- 3-methoxy-PREG decreases post-traumatic inflammation.

1. 3-Methoxy PREG Reaches the Brain Whatever the Type of Trauma

Previous studies in humans showed that TBI can change the clearance, the distribution volume and the metabolism of drugs (Empey et al., 2006; Marmarou et al., 2005). In order to establish whether TBI modifies the passage of 3-methoxy-PREG (MAP434) into the brain, MAP4343 was measured by liquid chromatography coupled to tandem mass spectrometry LC-MS/MS in the brain of animals sacrificed 6 h after CHI, LFP or CCI (4 h. after MAP4343 injection).

Results are displayed in FIG. 16 and show that concentrations of MAP4343 of significant therapeutic interest reach the brain of treated rats in all three trauma models.

2. 3-Methoxy-PREG Decreases the Anxiety Induced by Trauma:

The effect of 3-methoxy-PREG (MAP4343) on anxiety induced by trauma was analyzed using the WET test.

Results are displayed in Table 5 (day 7) and Table 6 (day 27) below and show that CCI trauma increases anxiety in traumatized animals at day 7 as well as day 27 post-trauma, as indicated by the decrease in the number of entries and the time spent in the CZ zone (see comparison of data obtained for control animals injected with sesame oil and for CCI traumatized animals injected with sesame oil)

This early then persistent anxiety induced by CCI trauma is alleviated by MAP4343 as early as day 7, in particular at the dose of 20 mg/kg (D2).

TABLE 5

Day 7: Entry number and time spent in the CZ in control animals injected with sesame oil (C-D0), and CCI traumatized animals injected from 24 hours post-trauma either with sesame oil (CCI-D0), or 10 mg/kg MAP4343 (CCI-D1) or 20 mg/kg MAP4343 (CCI-D2). Decrease in the number of entries or time spent in CZ indicates increased anxiety.

|  | C-D0 | CCI-D0 | CCI-D1 | CCI-D2 |
| --- | --- | --- | --- | --- |
| Entry number in CZ | | | | |
| Mean | 100 | 51 | 64 | 73 |
| Sem | 6 | 10 | 11 | 7 |

TABLE 5-continued

Day 7: Entry number and time spent in the CZ in
control animals injected with sesame oil (C-D0), and CCI
traumatized animals injected from 24 hours post-trauma either
with sesame oil (CCI-D0), or 10 mg/kg MAP4343 (CCI-D1) or
20 mg/kg MAP4343 (CCI-D2). Decrease in the number of
entries or time spent in CZ indicates increased anxiety.

|  | C-D0 | CCI-D0 | CCI-D1 | CCI-D2 |
|---|---|---|---|---|
| Conclusion vs. C-D0 | / | ↓↓↓ | / | / |
| Conclusion vs. CCI-D0 | / | / | ↔ | ↔ |
| Time spent in CZ | | | | |
| Mean | 100 | 35 | 48 | 66 |
| Sem | 9 | 7 | 11 | 11 |
| Conclusion vs. C-D0 | / | ↓↓↓ | / | / |
| Conclusion vs. CCI-D0 | / | / | ↔ | ↑ |

↓↓↓: decrease of analyzed variable with p < 0.001;
↔: stability of analyzed variable;
↑: increase in analyzed variable with p < 0.05.

TABLE 6

Day 27: Entry number and time spent in the CZ in
control animals injected with sesame oil (C-D0), and CCI
traumatized animals injected from 24 hours post-trauma either
with sesame oil (CCI-D0), or 10 mg/kg MAP4343 (CCI-D1) or 20 mg/kg
MAP4343 (CCI-D2). Decrease in the number of entries or
time spent in CZ indicates increased anxiety.

|  | C-D0 | CCI-D0 | CCI-D1 | CCI-D2 |
|---|---|---|---|---|
| Entry number in CZ | | | | |
| Mean | 100 | 62 | 79 | 114 |
| Sem | 11 | 14 | 16 | 16 |
| Conclusion vs. C-D0 | / | ↓ | / | / |
| Conclusion vs. CCI-D0 | / | / | ↔ | ↑↑ |
| Time spent in CZ | | | | |
| Mean | 100 | 59 | 86 | 95 |
| Sem | 18 | 15 | 37 | 19 |
| Conclusion vs. C-D0 | / | ↓ | / | / |
| Conclusion vs. CCI-D0 | / | / | ↔ | ↑ |

↓: decrease of analyzed variable with p < 0.05;
↔: stability of analyzed variable;
↑↑: increase in analyzed variable with p < 0.01.

3. 3-Methoxy PREG Reduces Ventricular Dilatation Induced by Trauma

MRI imaging of rats was performed at day 28 post-trauma. Based on MRI imaging, ventricular dilatation induced by CHI trauma was analyzed in CHI traumatized rats injected from 24 hours post-trauma with sesame oil (CHI-D0), or 3-methoxy-PREG (MAP4343) at 10 mg/kg (CHI-D1) or 20 mg/kg (CHI-D2).

Representative images are displayed in FIG. 17A, showing that CHI induces significant ventricular dilatation at day 28 post-trauma. The analysis of the MRI data confirm that MAP4343 significantly decreases the ventricular dilatation compared to the vehicle, if MAP4343 is injected at 20 mg/kg starting 24 hours post-trauma (see FIG. 17B showing ventricles areas of CHI traumatized animals injected with sesame oil (CHI-D0), or MAP4343 at 10 mg/kg (CHI-D1) or 20 mg/kg (CHI-D2)).

4. 3-Methoxy-PREG Protects the Hippocampus Size Integrity from the Legion Induced by Trauma The size of the CCI injured hippocampi is significantly smaller than that at non-injured hippocampi (see FIG. 18). 3-methoxy-PREG (MAP4343, 10 mg/kg-Dose 1 and 20 m/kg-Dose 2), with the first injection 2 h TBI, significantly increases the size of the injured hippocampus to level no longer different from the non-injured hippocampus (see FIG. 18).

5. 3-Methoxy-PREG Up-Regulates Neuronal Brain Markers of Plasticity

The expression level of various neuronal brain markers of plasticity was measured at day 35 post-trauma by western-blots in the cortex and hippocampus of left uninjured and right injured cerebral hemispheres of CCI traumatized animals receiving either vehicle (sesame oil, CCI-D0) or 3-methoxy-PREG (MAP4343) at 10 mg/kg (CCI-D1) or 20 mg/kg (CCI-D2), with first MAP4343 injection 2 h post-trauma.

The tested neuronal brain markers of plasticity included:
MAP2; the target of MAP4343 and a modulator of microtubule function (see FIG. 19),
Post-synaptic proteins: PSD95 (see FIG. 20) and spinophilin (see FIG. 21);
Pre-synaptic protein Synaptophysin (see FIG. 22);
Axonal growth/integrity protein GAP43 (see FIG. 23).

MAP2

It was previously reported that increased MAP2 expression and cytoskeleton stabilisation play a role in mediating enhanced functional outcomes after cerebral ischemia and SCI (Briones et al., 2006; Perez-Espejo et al., 1996). Previous reports showed that MAP2 was increased in the contralateral cortex and homotopic to unilateral cortical lesions in rats that underwent neuronal structural plasticity, such as dendrite addition (Hsu and Jones, 2006; Adkins et al., 2004; Jones and Schallert, 1992; Jones at al., 1999; Biernaskie and Corbett, 2001; Stroemer et al., 1995) and synaptogenesis (Luke et al., 2004; Hsu and Jones, 2005; Stroemer et al., 1995).

FIG. 19 shows that MAP2 expression is dramatically decreased in the injured cortex compared to uninjured cortex, and only slightly in injured hippocampus. Administration of 3-methoxy-PREG (MAP4343) at 20 mg/kg (CCI-D2), with first MAP4343 injection 2 h post-trauma, results in a strong increase of MAP-2 in the injured and non-injured brain (cortex and hippocampus).

Post-Synaptic Protein PSD95

PSD-95 is a postsynaptic density scaffold protein and one of the central organizers of synaptic adhesion that recruits diverse proteins to sites of synaptic adhesion, promotes trans-synaptic signaling, and couples neuronal activity with shanties in synaptic adhesion. Ansari et al., 2008 described the evolution of PSD95 in brain after TBI, and showed a significant time-dependent decline, ipsilaterally to the injury, at 48 h up to 96 h post-injury.

FIG. 20 confirms that 530-95 expression is decreased in injured cortex and hippocampus compared to uninjured cortex and hippocampus, respectively (compare expression in injured and non-injured cortex and hippocampus for CCI-D0). Administration of 3-methoxy-PREG (MAP4343) at 20 mg/kg (CCI-02), with first MAP4343 injection 2 h post-trauma, results in an increase in PSD95 expression . . . in the ipsilateral injured cortex and hippocampus, and also distantly to the lesion in the contralateral cortex (see FIG. 20).

Such an increased PSE-95 expression in MAP4343-treated rats Presumably correlates with an improved synaptic connectivity and neuronal networks (Lang et al., 2007) Indeed, PSD-95 is a core scaffolding component of post-synaptic elements, and is involved in synaptic function and neuronal plasticity. PSD-95 interacts with N-methyl-D-aspartate receptors (Gascon et al., 2007) and has important roles in the regulation of ion-channel functions, neuronal differentiation, synaptogenesis, synaptic plasticity, and the processes of learning and memory (Chen et al., 2007; Ehrlich et al., 2007), PSD-95 induces membrane addition to polarized synaptic compartments, formation of cellular junctions, synaptic protein anchoring, and trafficking (Tsuriel et al., 2006). PSD95, together with other synaptic proteins, plays a dynamic role in learning and memory (Wu et al., 2006; Gorczyca at al., 2007).

Post-Synaptic Protein Spinophilin

Spinophilin is a protein highly enriched in dendrites spines and involved in spine morphology and synaptic plasticity. Hu et al., (2010) suggest a possible role for spinophilin in neuronal plasticity induced by environmental enrichment.

FIG. 21 shows that spinophilin expression is highly decreased in inured cortex and hippocampus compared to uninjured cortex and hippocampus, respectively (compare expression in injured and non injured cortex and hippocampus for CCI-D0). Administration of 3-methoxy-PREG (MAP4343) at 10 mg/kg (CCI-D1) or 20 mg/kg (CCI-D2), with first MAP4343 injection 2 h post-trauma, results in an increase in spinophilin expression in the injured cortex and hippocampus and also contralaterally (see FIG. 21). This may Indicate increased dendritic spine remodelling in injured cortex and hippocampus of CCI traumatized animals receiving MAP4343.

Pre-Synaptic Protein Synaptophysin

Synaptophysin is a synaptic vesicle glycoprotein present in neuroendocrine cells and in virtually all neurons in the brain and spinal cord that participate in synaptic transmission. It acts as a marker for the quantification of synapses. Synaptophysin expression is significantly decreased after TBI (Ding et al., 2009). The exact function of the protein is unknown: it interacts with the essential synaptic vesicle protein synaptobrevin, but when the synaptophysin gene is experimentally inactivated in animals, they still develop and function normally. Recent research has shown, however, that elimination of synaptophysin in mice creates behavioral changes such as increased exploratory behavior, impaired object novelty recognition, and reduced spatial learning.

FIG. 22 shows that Synaptophysin expression is decreased in injured cortex and hippocampus compared to uninjured cortex and hippocampus, respectively (compare expression in injured and non-injured cortex and hippocampus for CCI-D0). Administration of 37-methoxy-PREG (MAP4343) at 20 mg/kg (CCI-D2), with first MAP4343 injection 2 h post-trauma, results in an increase in Synaptophysin expression in injured hippocampus (see FIG. 22).

Restoration of Synaptophysin expression level in injured hippocampus suggests increased neuronal plasticity in injured hippocampus of animals treated with MAP4343 at 20 mg/kg, with first MAP4343 injection 2 h post-trauma.

Axonal Growth/Integrity Protein GAP43 (Growth Associated Protein 43)

GAP-43 is a marker of axonal growth/axonal integrity and is considered a crucial component of the axon and presynaptic terminal. It is considered to play a key role in neurite formation, regeneration, and plasticity (Benowitz and Routtenberg, 1997), GAP-43 has been termed 'growth' or 'plasticity' protein because it is expressed at high levels in neuronal growth cones during neuronal development and axonal regeneration. It has been shown to be important also for the maintenance of the structure of axonal fibres and of their synaptic terminals both during normal conditions and during lesion-induced axonal sprouting (Grasselli et al., 2011). GAP-43 expression is decreased in injured cortex and hippocampus compared to uninjured cortex and hippocampus, respectively (compare expression in injured and non-injured cortex and hippocampus for CCI-D0) (FIG. 23). Administration of 3-methoxy-PREG (MAP4343) at 10 mg/kg (CCI-D1) 20 mg/kg (CCI-D2), with first MAP4343 injection 2 h post-trauma, results in as increased GAP-43 expression in injured cortex (20 mg/kg only) and hippocampus and also contralaterally in the non-injured cortex (both doses, see FIG. 23).

3-Methoxy-PREG Decreases Post-Traumatic Inflammation

Glial fibrillary acidic protein (GFAP) is an intermediate filament (IF) protein that was thought specific for astrocytes in the central nervous system (CNS). Later on, it was shown that GFAP is expressed in several cell types in CNS, including ependymal cells and astrocytes. It is involved in many cell functions, such as cell structure and movement, cell communication, and functioning of the blood brain barrier, but its exact function remains poorly understood, despite numerous studies using it as cell marker. GFAP is used as a marker of astrocytes immunoreactivity, and thus of brain inflammation. Many reports demonstrated GFAP up-regulation after brain and spinal, cord trauma (Newcomb et al., 1997).

GFAP expression was measured by immunohistochemistry at day 35 post-trauma in injured and uninjured cortex, thalamus and hippocampus of LFP traumatized, rats treated with vehicle (sesame oil), or 3-methoxy-PREG (MAP4343) at 10 mg/kg or 20 mg/kg, with first injection at 2 hours post-trauma.

In animals injected with vehicle, an increase of astrocytes immunoreactivity (GFAP expression) is noticed in the injured cortex just below the injury site; and in the injured thalamas, although the immunoreactivity is more diffuse than in the injured cortex. No difference in GFAP immunoreactivity is observed in the hippocampus between injured and non-injured sides.

Results obtained in animals treated with MAP4343 at 10 mg/kg or 20 mg/kg are displayed in FIG. 24A (cortex) and FIG. 24B (thalamus), and show that astrocytes GFAP immunoreactivity in the injured cortex is highly decreased in MAP343-injected animals, indicating that MAP4343 appears to decrease post-traumatic inflammation. In the injured thalamus, MAP4343 and especially Dose2 (20 mg/kg), strongly decreases astrocytes immunoreactivity at a level close to the one of non-injured thalamus, suggesting again that MAP4343 appears to decrease post traumatic inflammation.

CONCLUSION

MAP4343 treatment improves several crucial functional and biological outcomes of animals suffering a TBI, whether mild or severe, focal or diffuse, as modelled in 3 distinct experimental sorts of TBI. MAP4343-interacting MAP2 protein associated to cytoskeleton protection, remodelling of dendrites and axons, enhanced synaptic plasticity, are hallmarks and a possible part of mechanism of this recovery.

It is interesting and important to note, that the biochemical signatures of neuro-protection and/or neuro-reparation occur at the site of the lesion and also distantly to the lesion. MAP4343 is a proposed new treatment for all TBI situations, whatever the initial sort of trauma and degree of severity, with the medical objective of improving short-term as well as long-term post-traumatic consequences.

BIBLIOGRAPHIC REFERENCES

Adkins D L, et al. Neuroscience, 2004. 128, 473-486.
Andrade et al., Int J Methods Psychiatr Res. 2003; 12(1):3-21
Ansari M A, et al, J Neurotrauma. 2008 May; 25(5):513-26;
Benowitz L I, Routtenberg A. Trends Neurosci. 1997, 20 (2) 84-91;
Besson V C, et al. Brain Res. (2003) 989:58-66
Bianchi et al., Synapse 2003 Sep. 1; 49(3):188-94
Bianchi et al. (2005), Curr. Drug Targets CNS Neurol. Disord., 4:597-611;
Bianchi et al. (2006), Eur. J. Neurosci., 24:2894-2902
Biernaskie J, Corbett D., J. Neurosci, 2001, 21, 5272-5280.
Blier and de Montigny, Trends Pharmacol 1994 July; 15(7): 220-6;
Briones T L, et al. Behav Brain Res. 2006 Apr. 3; 168(2):261-71.
Brody D L et al. J Neurotrauma. 2007 April; 24(4):657-73;
Caceres et al., Neuron 1992 October; 9(4):607-18;
Campbell end Macqueen, J. Psychiatry Neurosci. 2004 November; 29(6):417-26;
Chen P, et al. Mol. Pharmacol. 2007; 72:40-51;
Cryan et al., Neurosci Biobehav Rev. 2005; 29(4-5):547-69;
Dellu et al. 1992, Brain Res., 588, 132-9
Dina J Y, et al. Brain Res. 2009 May 1; 1268:125-34;
Donati and Rasenick, Neuropsychopharmacology 2005 July; 30(7); 1238-45;
Egeland et al., Scand. J. Psychol. 2005 April; 46(2):201-8;
Ehrlich I, et al. Proc. Natl. Acad. Sci. U. S. A 2007; 104: 4176-4181;
Empey et al J. Neurotrauma. 2006 January; 23(1):109-16;
Ennaceur and Delacour, Behav Brain Res. 1988 Nov. 1; 31(1):47-59;
FARES Raafat P. Erythropoietin and enriched housing in Marlau™ cages protects, neurons and cognitive function in epileptic rats. PhD thesis of Dec. 22, 2009,
Garcia-Estrada et al., Int J Dev Neurosci. 1999 April; 17(2): 145-51;
Gascon S, et al. Mol. Psychiatry. 2008 January; 13(1):99-114. Epub 2007 May 8;
George et al., Biol Psychiatry. 1994 May 15; 35(10):775-80;
Gorczyca D, et al. J. Neurosci. 2007; 27: 1033-1044;
Götz, EMBO J. 1995; 14(7):1304-13
Gozes et al., CNS Drug Rev. 2005 Winter; 11(4):353-68
Grasselli G, et al. PLoS ONE, 2011, 6 (6);
Gursoy et al., Neurochem Res. 2001 January; 26(1):15-21
Guth et al., Proc Nat. Acad. Sci USA 1994 Dec. 6; 91(25): 12308-12;
Harada et al., J. Cell. Biol. 2002 Aug. 5; 158(3):541-9;
Holtzer S, et al. Crit Care Med. 2001 August; 29(8):1609-14.
Hsu J E, Jones T A. Eur. J. Neurosci. 2005. 22, 2069-2080.
Hsu J E, Jones T A. Exp Neurol. 2006 October; 201 (2):479-94.
Hu X L, et al. Neurosci Lett. 2010 May 31; 476(2):79-83;
Jones T A, Schallert T. Brain Res. 1992. 581, 156-160.
Jones T A, et al. J Neurosci 1999; 19:10153-63.
Kolb et al., Neuroscience 1997 February; 76(4):1139-51
Ladurelle et al. 2000, Brain Res., 858, 371-9
Lang S B, et al. J. Neurosci. 2007; 27:1097-1105;
Legrand and Alonso, Brain Res. 1998 Aug. 17; 802(1-2); 125-33;
Luduena, Int. Rev. Cytol. 1998 178:207-75;
Luke L M, et al. Synapse. 2004. 54, 187-199.
Malagiè et al., Eur. J. Pharmacol. 1995 Nov. 14; 286(2):213-7;
Manji et al., Nat. Med. 2001 May; 7(5):541-7;
Maria, Lancet 2002 Jul. 27; 360(9329):319-26;
Marmarou C R, et al. J. Neurotrauma. 2005 October; 22(10); 1066-80;
Matus, *Microtubules* 1994; edited by HYAMS and Lloyd, Wiley-liss (New York);
Meieran et al., Psychoneuroendocrinology 2004 May; 29(4); 486-500;
Mitchison and Kirschner, Neuron 1989 November; 1(9):761-72;
Miyamoto et al., Eur. J. Pharmacol. 1997 Aug. 27; 333(2-3): 279-87;
Murakami et al., Proc Natl Acad Sci USA 2000 Mar. 28; 97(7):3579-84;
Nakatomi et al., Cell 2002 Aug. 23; 110(4):429-41;
Newcomb J K, et al. Exp. Neurol. 1999. 158, 76-88;
Perez et al., Neuropsychopharmacology 1991 January; 4(1): 57-64;
Perez-Espejo M A, et al. Surg Neurol. 1996 October; 46(4): 350-7.
Remington's Pharmaceutical Sciences (Maack Publishing Co., Easton, Pa.
Reyna-Neyra et al., Brain Res. 2002 Sep. 30; 58(6):607-12;
Romero et al., *J. Neurochem.* 1997, June 68 (6:2593-603);
Sanchez et al., *Prog. Neurobiol* 2000, June 61, (2:133-68);
Schumacher et al., J Neurochem 2000 April; 74(4); 1646-55;
Serra et al. Psychopharmacology 2001 October; 158(1):48-54;
Serra et al., J. Neurochem. 2000 August; 75(2):732-40;
Springer et al., J Neurochem 1997 October; 69(4):1592-600;
Stroemer R P, et al. Stroke. 1995. 26, 2135-2144.
Thompson S N, et al. Exp Neurol. 2006 September; 201(1): 253-65.
Tsuriel S, et al. PLoS Biol. 2006; 4:e271
Vaillant et al., Neuron 2002 Jun. 13; 34(6):965-98;
Warner-Schmidt and Duman, Hippocampus 2006 16(3):239-49;
Weiss and Feldon, Psychopharmacology 2001 July; 156(2-3):305-26;
WO 00/32236
Wu A. et al. Exp. Neurol. 2006; 197:309-317
Zhang et al., *J Neuropathol Exp Neurol* 2000, April 59 (4: 287-96).

The invention claimed is:

1. A method for the treatment of a cerebral lesion in patient in need thereof, comprising administering to said patient of an effective quantity of 3β-methoxy-pregna-5-ene-20-one (3β-methoxy-PREG).

2. The method according to claim 1, wherein the administration is by injection.

3. The method according to claim 1, wherein the administration is oral.

4. The method according to claim 1, wherein the quantity of 3β-methoxy-pregnenolone administered to said patient is ranging between 1 and 100 mg/kg body weight.

5. The method according to claim 2, wherein the quantity of 3β-methoxy-pregnenolone administered to said patient is ranging between 1 and 100 mg/kg body weight.

6. The method according to claim 3, wherein the quantity of 3β-methoxy-pregnenolone administered to said patient is ranging between 1 and 100 mg/kg body weight.

* * * * *